(12) United States Patent
McFarlane et al.

(10) Patent No.: US 6,707,307 B1
(45) Date of Patent: Mar. 16, 2004

(54) FLUID SENSOR

(75) Inventors: Ronald A. McFarlane, Victoria (CA); Gail S. Gabel, Victoria (CA)

(73) Assignee: ESI Environmental Sensors Inc., Victoria (CA)

( * ) Notice: Subject to any disclaimer, the term of this patent is extended or adjusted under 35 U.S.C. 154(b) by 0 days.

(21) Appl. No.: 09/642,015

(22) Filed: Aug. 21, 2000

(30) Foreign Application Priority Data

May 30, 2000 (CA) .............................................. 2310417

(51) Int. Cl.[7] ........................ G01R 27/26; G01R 27/28; G01R 27/04
(52) U.S. Cl. ........................ 324/664; 324/617; 324/639
(58) Field of Search .................................. 324/664, 637, 324/639, 629, 634, 640, 644, 642, 617, 618; 73/597

(56) References Cited

U.S. PATENT DOCUMENTS

| | | | |
|---|---|---|---|
| 3,025,464 A | 3/1962 | Bond ........................... | 324/61 |
| 3,200,312 A | 8/1965 | Callahan ...................... | 317/246 |
| 3,523,245 A | 8/1970 | Love et al. .................... | 324/61 |

(List continued on next page.)

FOREIGN PATENT DOCUMENTS

FR 2619253 2/1989 .............. H01P/5/00

OTHER PUBLICATIONS

Copy of International Search Report for International Application No. PCT/CA01/00788, mailed Apr. 22, 2002, 5 pages.
Mike Sly, Re: choose a sensor—TDT vs TDR, XP–002194861, retrieved from the Internet, http://www-.sowacs.com/archives/98–12/msg00021.html, dated Dec. 4, 1998, 3 pages.

W. J. Thompson, Virrib, XP–002194862, retrieved from the Internet, http://www.sowacs.com/archives/99–10/msg-00033.html, dated Oct. 31, 1999, 2 pages.
Automatic measuring of soil moisture, XP–002194863, retrieved from the Internet, http://www.chmi.cz/meteo/ok/oba/obs/epuda.html, retrieved Apr. 2, 2002, 3 pages.
J.L. Davis and A.P. Annan, Electromagnetic Detection of Soil Moisture: Progress Report I, Canadian Journal of Remote Sensing, vol. 3, No. 1, Dec. 1977, pp. 76–86.
Mohammad A. Saed et al., Wide–Band Measurement of the Complex Permittivity of Dielectric Materials Using a Wide–Band Cavity, IEEE Transactions on Instrumentation and Measurement, vol. 38, No. 2, Apr. 1989, pp. 488–495.
K.M. Fidanboylu et al., An Enhanced Time Domain Approach for Dielectric Characterization Using Stripline Geometry, Instrumentation and Measurement Technology Conference, Atlanta, May 14–16, 1991, IEEE 1991, pp. 641–647.

(List continued on next page.)

*Primary Examiner*—Anjan K. Deb
(74) *Attorney, Agent, or Firm*—Anthony R. Lambert

(57) ABSTRACT

A sensor for measuring the dielectric constant of a fluid uses time of flight measurements. The sensor has a conduit for the fluid, preferably a transmission line. The dielectric constant of the fluid affects tranmission of electrical energy along the transmission line. An electrical generator, having as output an electrical transient, is operably connected to one end of the transmission line for transmitting the electrical transient along the conduit, where propagation of the electrical conduit is affected by the fluid. A receiver is connected to the other end of the conduit for detecting electrical transients that have passed along the conduit from the electrical generator. A processor is operably connected to the electrical generator and to the receiver, the processor being programmed to cause an electrical transient to be generated by the electrical generator for passage along the conduit and determine the dielectric constant of the fluid from characteristics of the electrical transient detected at the receiver.

22 Claims, 32 Drawing Sheets

U.S. PATENT DOCUMENTS

| | | | |
|---|---|---|---|
| 3,768,007 A | * 10/1973 | Tozer | 324/84 |
| 3,853,005 A | 12/1974 | Schendel | 73/290 R |
| 3,965,416 A | * 6/1976 | Friedman | 324/633 |
| 3,995,212 A | 11/1976 | Ross | 324/58.5 B |
| 4,429,273 A | 1/1984 | Mazzagatti | 324/61 R |
| 4,559,493 A | 12/1985 | Goldberg et al. | 324/61 R |
| 4,769,593 A | 9/1988 | Reed et al. | 324/61 R |
| 4,774,680 A | 9/1988 | Agar | 364/550 |
| 4,786,857 A | 11/1988 | Mohr et al. | 324/58.5 B |
| 4,862,060 A | 8/1989 | Scott et al. | 324/58.5 |
| 4,864,850 A | 9/1989 | Price | 73/73 |
| 4,866,369 A | 9/1989 | Guillou et al. | 324/58 B |
| 4,996,490 A | 2/1991 | Scott et al. | 324/639 |
| 5,025,222 A | * 6/1991 | Scott et al. | 324/639 |
| 5,069,070 A | * 12/1991 | Schmitz | 73/597 |
| 5,101,163 A | 3/1992 | Agar | 324/639 |
| 5,101,367 A | 3/1992 | Agar | 364/551.01 |
| 5,103,181 A | 4/1992 | Gaisford et al. | 324/637 |
| 5,148,125 A | 9/1992 | Woodhead et al. | 331/135 |
| 5,157,339 A | * 10/1992 | Scott et al. | 324/639 |
| 5,315,258 A | 5/1994 | Jakkula et al. | 324/640 |
| 5,341,100 A | 8/1994 | Taylor | 324/341 |
| 5,351,521 A | 10/1994 | Cracknell | 73/19.1 |
| 5,444,379 A | * 8/1995 | Ohmi et al. | 204/408 |
| 5,459,403 A | 10/1995 | Kohler et al. | 324/643 |
| 5,503,004 A | 4/1996 | Agar | 73/61.44 |
| 5,554,936 A | 9/1996 | Mohr | 324/642 |
| 5,648,724 A | 7/1997 | Yankielun et al. | 324/533 |
| 5,723,979 A | 3/1998 | Mohr | 324/642 |
| 5,729,123 A | 3/1998 | Jandrasits et al. | 324/71.1 |
| 5,748,002 A | 5/1998 | Scott et al. | 324/633 |
| 5,818,241 A | 10/1998 | Kelly | 324/640 |
| 5,898,308 A | * 4/1999 | Champion | 324/643 |
| 5,926,024 A | 7/1999 | Blount et al. | 324/324 |
| 5,929,342 A | 7/1999 | Thompson | 73/861.04 |
| 6,060,889 A | 5/2000 | Hocker | 324/667 |

OTHER PUBLICATIONS

Knight, J.H., "Sensitivity of Time Domain Reflectometry Measurements to Lateral Variations in Soil Water Content," Water Resour. Res. V. 28, 1992, pp. 2345–2352.

Annan, A.P., "Time–Domain Reflectometry–Air–Gap Problem In A Coaxial Line", Report of Activities, Part B; Geol. Surv. Can., Paper 77–1B (1977), p. 55–58.

* cited by examiner

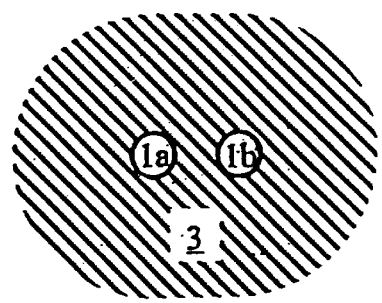 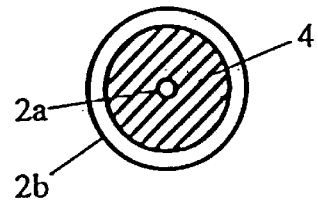
FIGURE 1A
FIGURE 1B
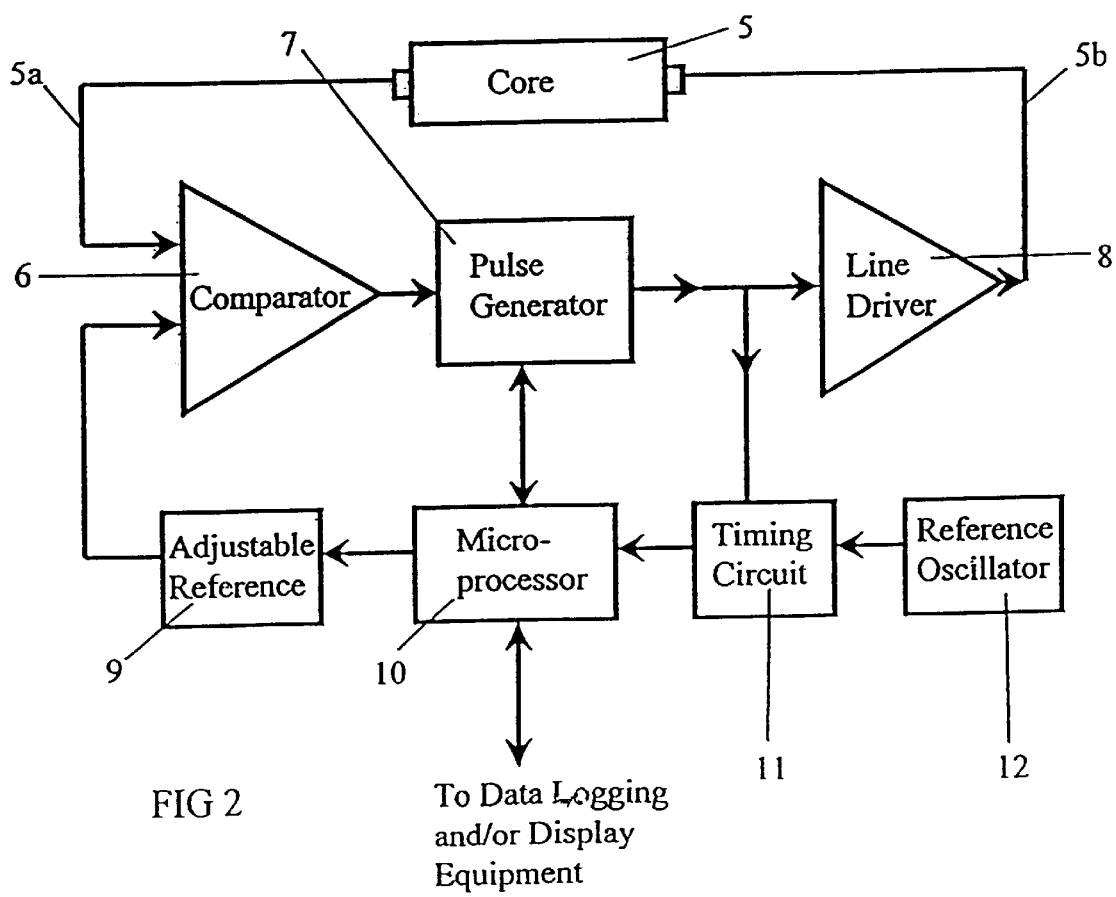
FIG 2
To Data Logging and/or Display Equipment

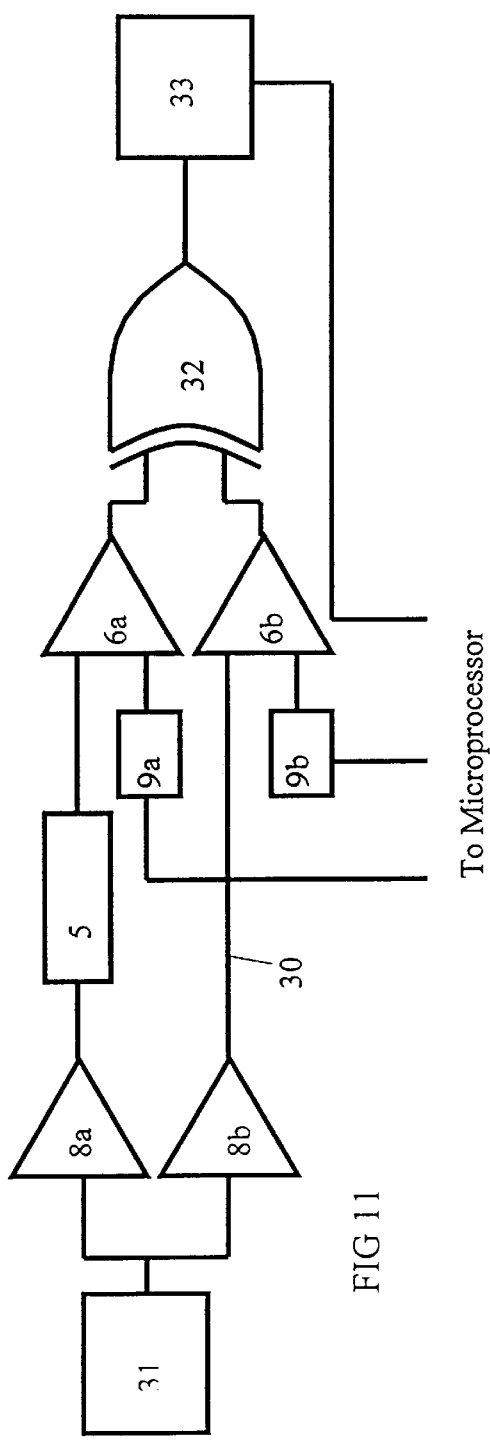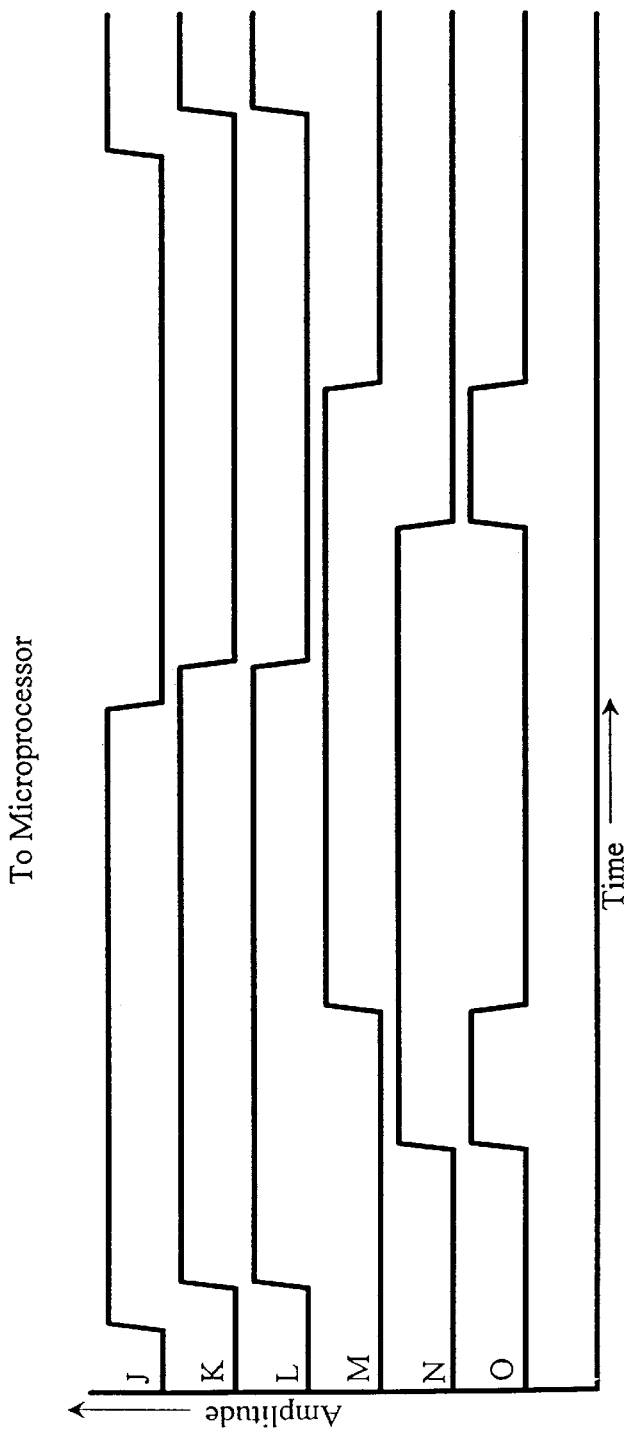

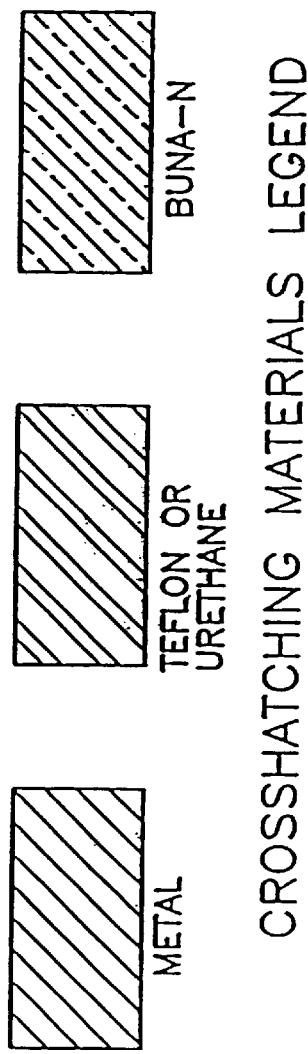
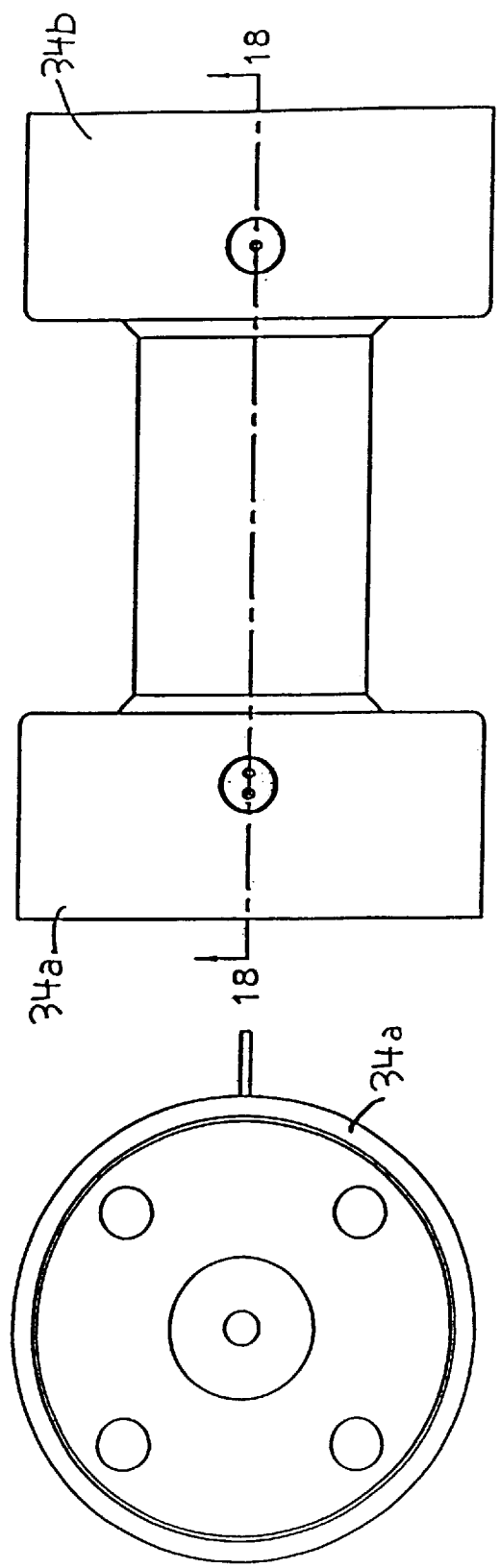
FIG 17A
FIGURE 17B

FLUID SENSOR

FIELD OF THE INVENTION

This invention relates to the measurement of the dielectric constant of a fluid mixture and specifically the measurement of the amount of water contained in an oil/water mixture.

BACKGROUND OF THE INVENTION

It is very useful to know the water content of an oil/water mixture for a number of applications in the petroleum industry. Measuring the water content of the oil emerging from an oil well can give an indication of the general health of the well and whether or not the well is being pumped too fast. Measuring the water content of oil emerging from a treating facility provides feedback on the efficiency of the treating operation. And, measuring the water content of oil at the point of custody transfer assures the buyer and seller of the quantities of oil and water being transferred.

The prior art contains a number of instruments for producing such a measurement. A number of these devices rely on somehow measuring the dielectric constant of the oil/water mixture. Because the relative dielectric constant of oil is in the range of 2 to 3 and that of water is approximately 80 the presence of water in the oil has a significant effect on the dielectric constant of the mixture.

One such method for measuring the dielectric constant is the capacitance method. Devices covered by U.S. Pat. No. 3,200,312 to Callahan, U.S. Pat. No. 3,025,464 to Bond, U.S. Pat. No. 3,523,245 to Love et al, U.S. Pat. No. 5,929,342 to Thompson, and U.S. Pat. No. 4,774,680 to Agar are examples of this method applied to the measurement of water in oil/water mixtures. Other applications to which the capacitance method is applied to determine water content can be seen in U.S. Pat. No. 4,769,593 to Reed et al, U.S. Pat. No. 4,864,850 to Price, and U.S. Pat. No. 4,559,493 to Goldberg et al.

Another class of methods for determining the water content involves the use of microwaves. There are a few different ways that microwaves can be used.

U.S. Pat. No. 5,103,181 to Gaisford et al describes a device in which the oil/water mixture is made to flow through a section of pipe that has been modified to look like a resonant cavity. Microwave energy is introduced into the container and forms constructive and destructive interference at various positions within the cavity. Two microwave detectors are positioned at the side of the container at predetermined positions. The frequency of the microwave energy is adjusted until the phase of the signal at each receiver is exactly in phase or out of phase. The frequency at which this occurs is used to deduce the dielectric constant of the fluid within the resonant cavity.

U.S. Pat. No. 5,101,163 to Agar describes a form of microwave sensor similar to Gaisford et al. Agar places the microwave transmitter and two microwave receivers within a pipe containing the fluid to be measured. The pipe acts as a microwave waveguide instead of a resonant cavity. The receivers are positioned on either side of the transmitter at specified distances from the transmitter. The transmitter emits microwave energy into the waveguide. This energy is received by the receivers. The frequency of the microwave energy is adjusted until the signals at the receivers are in phase or out of phase. The frequency at which this occurs is used to deduce the dielectric constant of the fluid within the pipe.

U.S. Pat. Nos. 4,862,060; 4,996,490; 5,025,222; 5,157,339; and 5,748,002 to Scott et al describe the use of microwave load pulling to determine the dielectric constant of the oil/water mixture. The fluid to be tested flows through a resonant cavity. A microwave oscillator is electrically coupled to the resonant cavity. The dielectric constant of the fluid in the cavity alters the resonant characteristics of the cavity. The change in the frequency and amplitude of the microwave oscillations is used to deduce the dielectric constant of the fluid within the resonant cavity.

U.S. Pat. No. 5,926,024 to Blount et al describes a system similar to that of Scott et al that has been modified to work in down-hole applications.

U.S. Pat. No. 5,351,521 to Cracknell describes another method of using microwaves to deduce the dielectric constant of an oil/water mixture within a pipe. One or more pipe sections, each having a diameter smaller than the pipe containing the mixture, are inserted into the pipe. Microwave energy is transmitted along the pipe, through the smaller pipe sections, to a receiver. The pipe and pipe sections act as a waveguide. Thus, this geometry has an upper limit to the wavelength it will allow to propagate. The frequency of the microwave energy is lowered, increasing the wavelength until the receiver stops receiving the energy. This cutoff frequency is related to the geometry of the pipe and pipe sections and the dielectric constant of the fluid filling the pipe.

Another method of determining the water content involves the use of time domain reflectometry or TDF Generally, a TDR instrument consists of a signal source capable of supplying a voltage step with a very short rise time or voltage pulse with very short transition times, a transmission line, a probe that somehow interacts with the physical variable to be measured, and a timing circuit. The operation of the instrument consists of generating the signal propagating the signal along the transmission line to the probe, having the probe reflect the signal in some fashion, propagating the reflected signal back to the signal source, and measuring the interval of time between the generation of the signal and the return of the reflected signal. The probe can be fashioned to interact with one or more physical parameters. Two of these parameters are dielectric constant and fluid level.

If a known length of the probe is immersed in the material to be measured, the material not necessarily being an oil/water mixture, the measured time interval can be used to deduce the propagation velocity of the signal along the portion of the probe immersed in the material. This propagation velocity can, in turn, be used to deduce the dielectric constant of the material surrounding the probe. Examples of this kind of sensor are given in U.S. Pat. No. 3,965,416 to Friedman, U.S. Pat. No. 3,995,212 to Ross, U.S. Pat. No. 4,786,857 to Mohr et al, U.S. Pat. No. 5,459,403 to Kohler et al, U.S. Pat. No. 5,554,936 to Mohr, U.S. Pat. No. 5,723,979 to Mohr, U.S. Pat. No. 5,729,123 to Jandrasits et al, U.S. Pat. No. 5,818,241 to Kelly, and U.S. Pat. No. 5,898,308 to Champion.

U.S. Pat. No. 4,429,273 to Mazzagatti describes a probe geometry for an oil/water monitor. Mazzagatti briefly mentions two kinds of excitations that may be used with this geometry, but does not reveal the details of the monitoring means.

SUMMARY OF THE INVENTION

According to an aspect of the invention there is provided a method of determining a property of a fluid, such as water content of a hydrocarbon stream, that involves the use of time domain transmissometry or TDT. In TDT, the signal of interest enters the probe or sensor via one port, interacts with the fluid to be measured as it travels along the probe, and exits the probe via another port.

TDT has two main advantages over TDR. First, the signal only travels along the probe once in TDT whereas it makes two transits of the probe in TDR In cases where the bulk electrical conductivity of the fluid to be measured is high, the propagation losses of the signal while it travels along the probe will be high. In the case of TDR the signal must propagate a distance that is twice that of TDT so the losses will be at least a factor of 2 larger. Second, the receiver for a TDR instrument must distinguish the reflection of interest from a variety of other reflections caused by the system. When the amplitude of the reflected signal of interest is low this distinction can be difficult, even for a trained human observer. In the case of TDT, the first signal reaching the receiver is the signal of interest. Any subsequent reflected signals reaching the receiver are much less of a concern.

Therefore, there is provided a sensor for measuring the dielectric constant of a fluid, the sensor comprising:
  a conduit for the fluid, the conduit having first and second ends, between which electrical energy may pass;
  an electrical generator having as output an electrical transient, the electrical generator being operably connected to the first end of the conduit for transmitting the electrical transient along the conduit, wherein propagation of the electrical conduit is affected by the fluid;
  a receiver connected to the second end of the conduit for detecting electrical transients that have passed along the conduit from the electrical generator; and
  a processor operably connected to the electrical generator and to the receiver, the processor being programmed to cause an electrical transient to be generated by the electrical generator for passage along the conduit and determine the dielectric constant of the fluid from characteristics of the electrical transient detected at the receiver.

According to a further aspect of the invention, the conduit is a transmission line, the transmission line having a dielectric arranged so that the dielectric of the transmission line includes the fluid to be measured.

According to a further aspect of the invention, the conduit is preferably enclosed within a pressure container.

According to a further aspect of the invention, a characteristic of the electrical transient used by the processor is the time interval between the generation of the electrical transient by the electrical generator and the reception of the electrical transient at the receiver.

According to a further aspect of the invention, the electrical generator generates a further electrical transient upon receipt of an electrical transient at the receiver, thereby forming a sing-around circuit, and the sensor further comprises a timing circuit for measuring the oscillation period of the sing-around circuit, the timing circuit being configured to output a timing signal to the processor.

According to a further aspect of the invention, the sensor is provided with a reference circuit that has similar electrical delay to the sensor components, but is not affected by the fluid to be measured. In this aspect, the processor is configured to determine the dielectric constant of the fluid taking into account delay of the electrical transient due to passage through electrical components that are common to both the sensor and the reference circuit.

According to a further aspect of the invention, the transmission line is formed from co-axial inner and outer conductors, and has an annulus between the inner and outer conductors, with fluid to be measured filling the annulus.

According to a further aspect of the invention, the outer conductor forms a wall of the container. According to a further aspect of the invention, the transmission line comprises first and second parallel side-by-side conductors separated by a gap, the gap being substantially filled by the fluid to be measured.

According to a further aspect of the invention, the one or both of the conductors is coated with one or more layers of electrical insulation, and preferably the electrical insulation extends a distance into the annulus (or across the gap) sufficient to exclude fluid being measured from areas of greatest electric field intensity. A top layer should be selected for its insulation capabilities, while lower layers may be selected for ease of providing a thick layer.

According to a further aspect of the invention, the receiver, and also the second receiver in the core, comprises a comparator for comparing the voltage level of signals received by the receiver with an adjustable threshold, the time of arrival of the electrical transient being the time at which the voltage level of signals received by the receiver exceeds the threshold.

According to a further aspect of the invention, the processor is programmed to:
  A) adjust the adjustable threshold to a value that is below the maximum voltage level of the electrical transient received by the receiver;
  B) determine the travel time of the electrical transient along the transmission line for the adjusted value of the adjustable threshold;
  C) repeat steps A and B for different values of the adjustable threshold to form a set of data pairs comprising the adjustable threshold and the travel time for each setting of the adjustable threshold; and
  D) determine the dielectric constant and the bulk conductivity of the fluid being measured from the data pairs.

According to a further aspect of the invention, the processor is programmed to find a curve that matches the data pairs, determine the bulk conductivity of the fluid being measured from an extrapolation of the curve at a travel time corresponding to the base line of the electrical transient and correct the time interval using the determined bulk conductivity of the fluid.

According to a further aspect of the invention, there is provided a sensor having improved selectivity of transmission modes along the transmission line. According to this aspect of the invention, there is provided a sensor for determining a property of a fluid, the sensor comprising:
  a transmission line extending between a first end and a second end, the transmission line being defined by co-axial inner and outer conductors, the inner and outer conductors being spaced apart to define a gap through which gap a fluid may flow;
  an electrical generator connected through a distributed connection to the transmission line for transmitting electromagnetic energy into the transmission line;
  a receiver operably connected to the transmission line for receiving electromagnetic energy that has passed along the transmission line from the electrical generator; and
  a processor connected by first and second communication links respectively to the electrical generator and the receiver for processing signals received by the receiver and for generating a signal indicative of a property of fluid confined within the gap from signals received by the receiver that have passed along the transmission line.

According to a further aspect of the invention, the property is the dielectric constant of the fluid, and the processor is programmed to calculate the dielectric constant of the fluid from the time of flight of electrical signals along the transmission line.

According to a further aspect of the invention, the distributed connection comprises first and second feed lines, preferably in the form a co-axial cables, the first feed line being electrically connected to the inner conductor, and the second feed line being electrically connected to the outer conductor, and the second feed line being electrically connected to the outer conductor at multiple positions around the outer conductor.

According to a further aspect of the invention, the second feed line is electrically connected to the outer conductor at least at three positions.

According to a further aspect of the invention, the connection positions are spaced uniformly around the outer conductor.

These and other aspects of the invention are described in the detailed description of the invention and claimed in the claims that follow.

BRIEF DESCRIPTION OF THE DRAWINGS

There will now be described preferred embodiments of the invention with reference to the drawings, by way of illustration only, and without intending to limit the invention to the precise embodiments disclosed, in which like reference characters denote like elements and in which:

FIGS. 1A and 1B are cross-sections of two types of transmission lines, with parallel conductors in FIG. 1A and co-axial conductors in FIG. 1B.

FIG. 2 shows a functional block diagram of the components that are required to implement the sing-around scheme according to one aspect of the invention.

FIG. 11 shows an alternative electronic circuit that can be used instead of the sing-around circuit.

FIG. 12 is a graph showing the timing relationship of the signals generated in circuit of FIG. 11.

FIGS. 17A and 17B show respectively a plan view and end view of the outside of an alternate device configuration which utilizes a parallel transmission line.

DESCRIPTION OF PREFERRED EMBODIMENTS

The device measures the water content of an oil stream by measuring the apparent dielectric constant of the stream. Water has a dielectric constant of ~80 at room temperature whereas oil has a dielectric constant in the range of 2 to 4. Therefore, the presence of water in the oil greatly affects the apparent dielectric constant of the oil/water mixture.

The device measures the apparent dielectric constant of the stream by measuring the time of flight of an electromagnetic wave propagating in intimate contact with the oil stream. Electromagnetic waves can propagate through free space, through a wave-guide, or along a transmission line. The time of flight measurement principle can be applied to all three of these cases. The preferred embodiment utilizes a transmission line.

A transmission line consists of two electrical conductors separated by a dielectric. By arranging that the oil stream becomes all or part of the dielectric between two conductors, variations in the apparent dielectric constant of the oil stream will affect the propagation characteristics of the transmission line. The two most common forms of transmission line are the parallel conductor and coaxial, both shown in cross-section in FIGS. 1A and 1B.

In the coaxial geometry the oil stream forms the dielectric between the inner and outer conductors. As the water content of the oil stream varies the dielectric of the coaxial transmission line changes. The speed at which electromagnetic waves propagate along a coaxial transmission line is inversely proportional to the square root of the dielectric constant of the dielectric material between the inner and outer conductors. In other words, the time required for an electromagnetic wave to propagate along a given length of coaxial transmission line is directly related to the water content of the oil stream.

In the parallel conductor geometry the oil stream forms the dielectric between and around the conductors. The water content of the oil stream affects the propagation properties of this geometry in a manner similar to that of the coaxial geometry. The field of influence of this geometry is confined to an area close to the conductors and between the conductors. For this reason it is useful to encase the conductors in a non-conducting dielectric which confines the flow of oil to the area between the conductors.

Figure 14A:
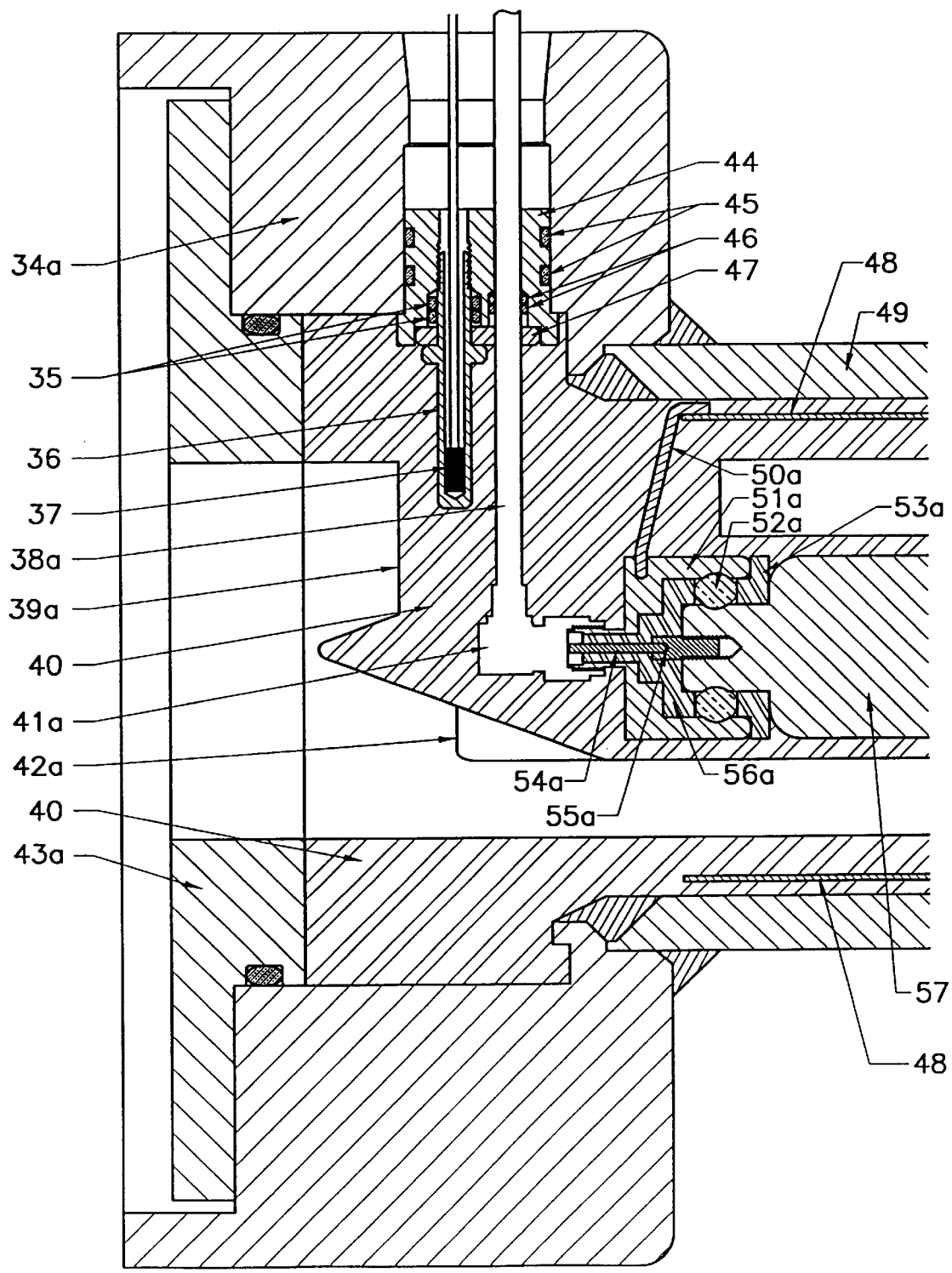
FIG. 14A and FIG. 14B together show a cross section 14 of an embodiment of the invention.
Figure 14B:
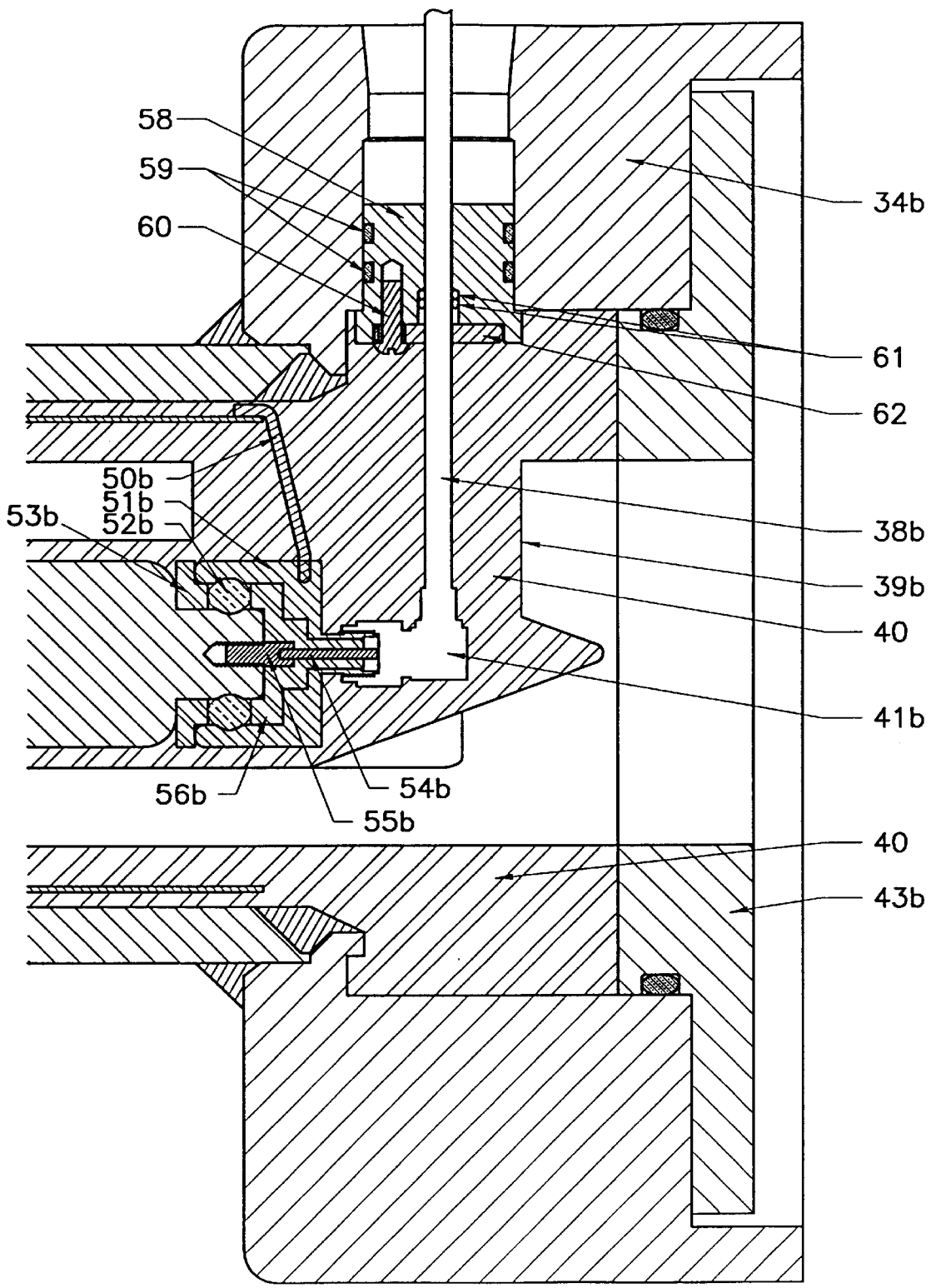
Figure 18A:
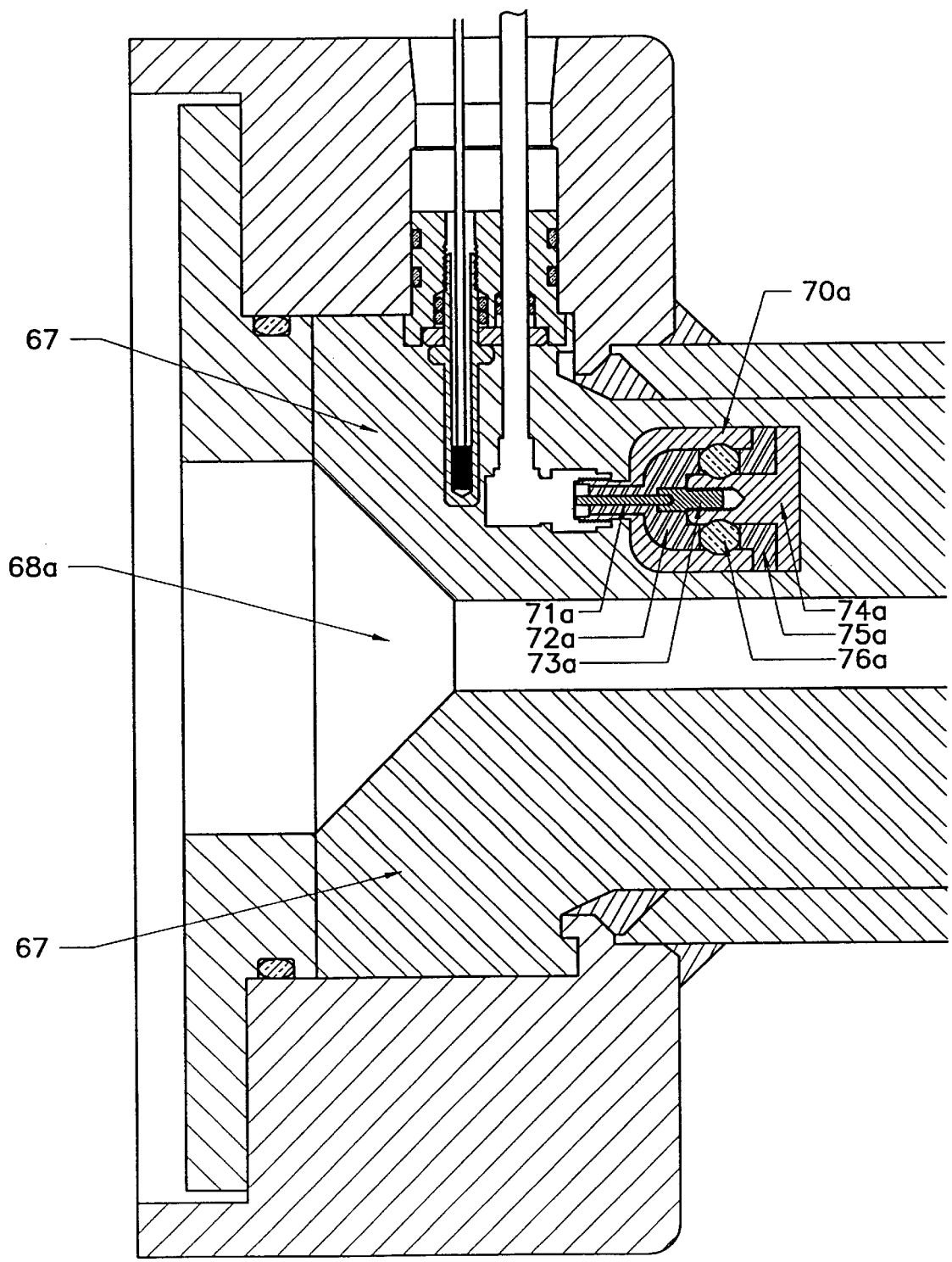
FIG. 18A and FIG. 18B together show a cross section 18 of an alternate embodiment of a device according to the invention.
Figure 18B:
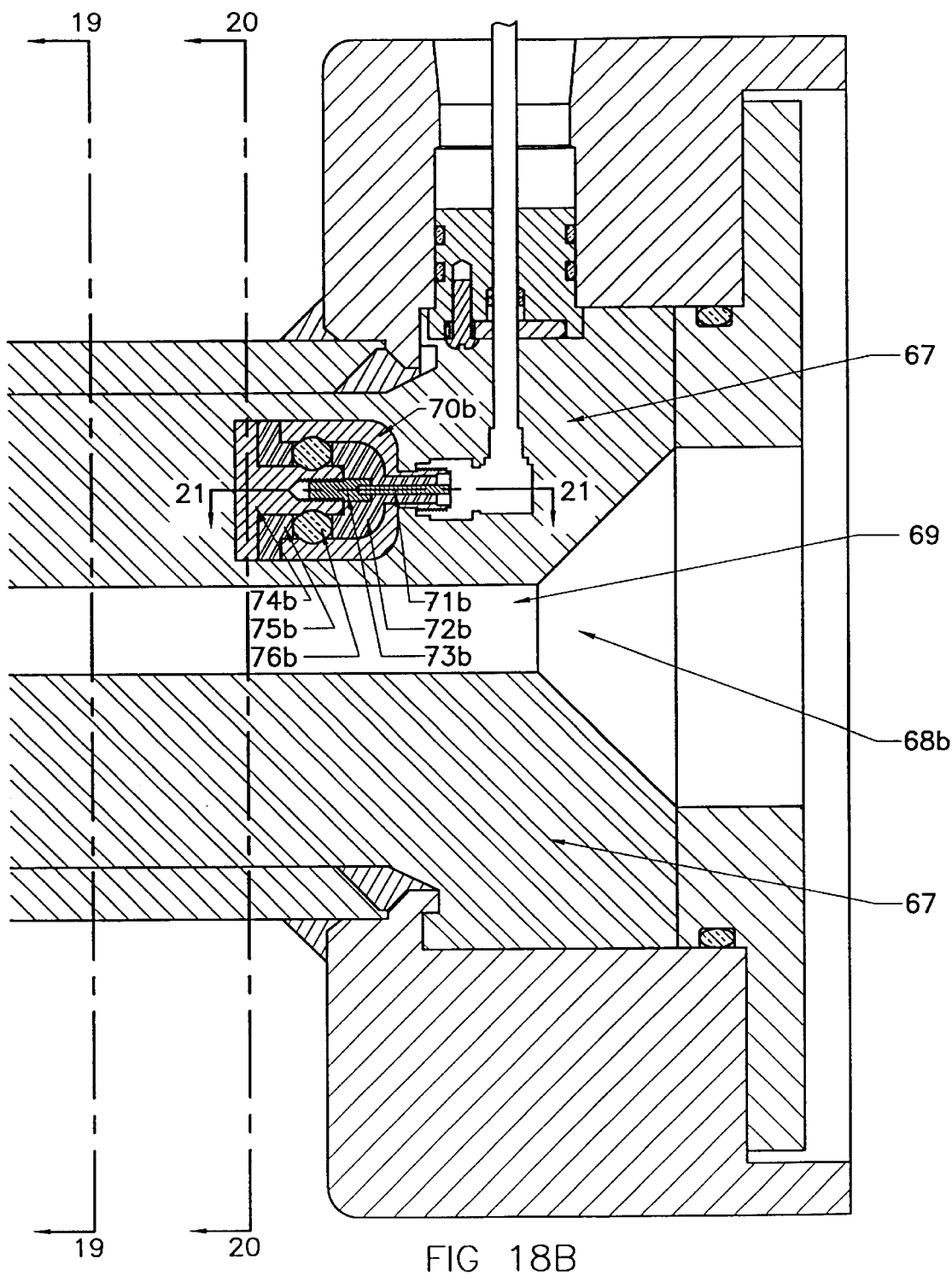
Figure 19:
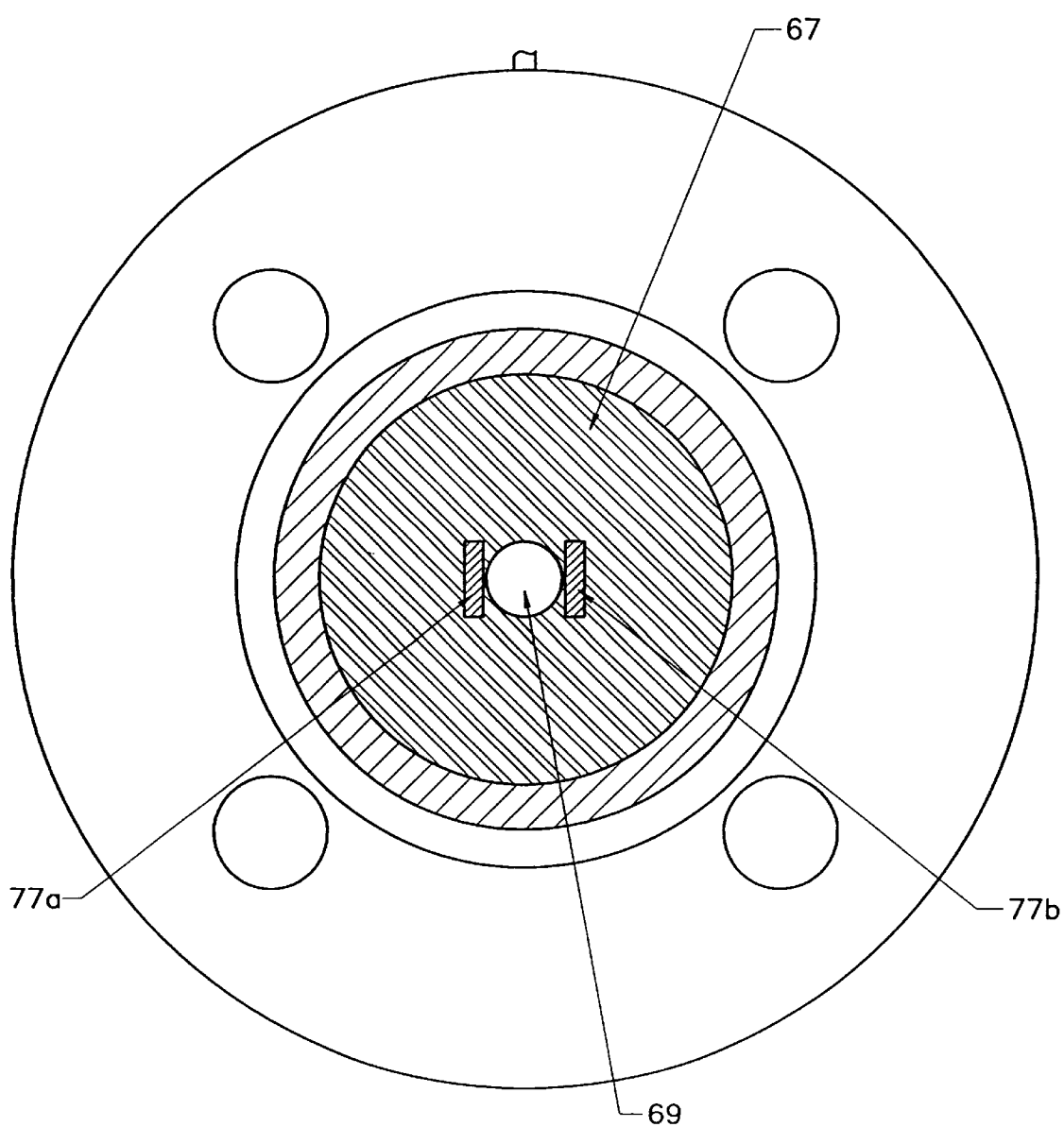
FIG. 19 shows a cross section 19 of the embodiment of FIGS. 18A and 18B.

For the purposes of this description, the term core is used to refer to both of the following collection of parts:

1) With respect to the coaxial geometry, and referring to FIG. 14A and FIG. 14B, the outer conductor 48, the inner conductor 57, and the spider assemblies, consisting of the spider bodies 51a and 51b, washers 53a and 53b, inserts 56a and 56b, SMA center contacts 54a and 54b, contact plugs 55a and 55b, spider legs 55a and 55b, and sealing o-rings 52a and 52b 2) With respect to the parallel conductor geometry, and referring to FIG. 18A, FIG. 18B and FIG. 19, both transmission line conductors 77a and 77b, and the transition assemblies, each transition assembly consisting of the outer transition body 70a and 70b that connects to conductor 77a, inner transition body 74a and 74b that connect to conductor 77b, washer 75a and 75b, spacer 72a and 72b, SMA center contact 71a and 71b, contact plug 73a and 73b, and sealing o-ring 76a and 76b.

The preferred embodiment of the sensor consists of the core secured inside a pressure pipe, an electronics package to measure the speed of propagation of an electromagnetic wave through the core, and conventional coaxial cables connecting the electronics package to the core.

Referring to the Figures, FIGS. 1A and 1B show the cross-sections of the two types of transmission lines. In both cases there exists a pair of conductors that run perpendicular to the plane of the page. Items 1a and 1b are the conductors of a parallel side-by-side conductor transmission line. Item 3 is the dielectric material surrounding the conductors. Items 2a and 2b are the conductors of a coaxial transmission line. Item 4 is the dielectric material occupying the space between the inner conductor 2a and the outer conductor 2b.

FIG. 2 shows a functional block diagram of the components that are required to implement the sing-around scheme. The core 5 is the section of the device consisting of the portion of the transmission line that interacts with the fluid to be measured, together with the fluid to be measured. The pulse generator 7 generates a pulse in response to a signal from either the comparator 6 or the microprocessor 10. The line driver 8 amplifies the pulse generated by the pulse generator 7 and launches it into the transmission line 5b (or other communication link) connecting the core 5 to the line driver 8. The comparator 6 receives the pulse from the transmission line Sa (or other communication link) connecting the comparator 6 to the core 5. The adjustable voltage reference 9 is set by the microprocessor 10 and supplies the reference to the other input of the comparator 6. The timing circuit 11 receives a signal from the pulse generator 7 and compares the period of oscillation of the pulse generator 7 to that of the reference oscillator 12. The results of this comparison are transmitted to the microprocessor 10.

Figure 3:
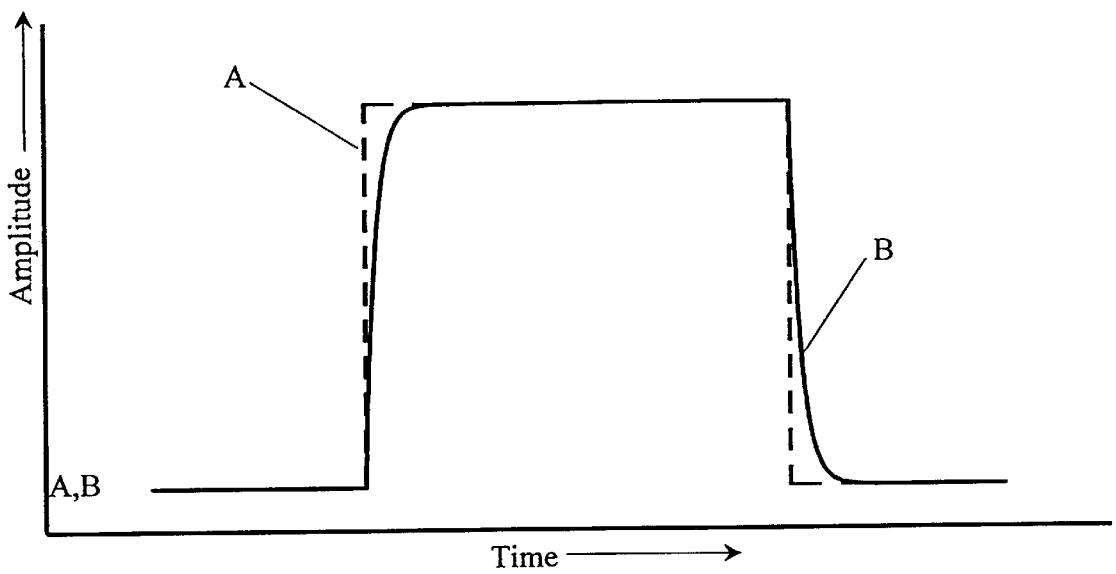
FIG. 3 is a graph comparing two waveforms A and B. A depicts the shape of an ideal pulse while B depicts the shape of a real pulse including the affect of finite rise and fall times.

FIG. 3 compares two waveforms A and B. A depicts the shape of an ideal pulse while B depicts the shape of a real pulse including the affect of finite rise and fall times. Any electrical transient such as a pulse or rising edge may be used in the operation of the invention. The electrical transient is generated by the electrical generator 7.

Figure 4:
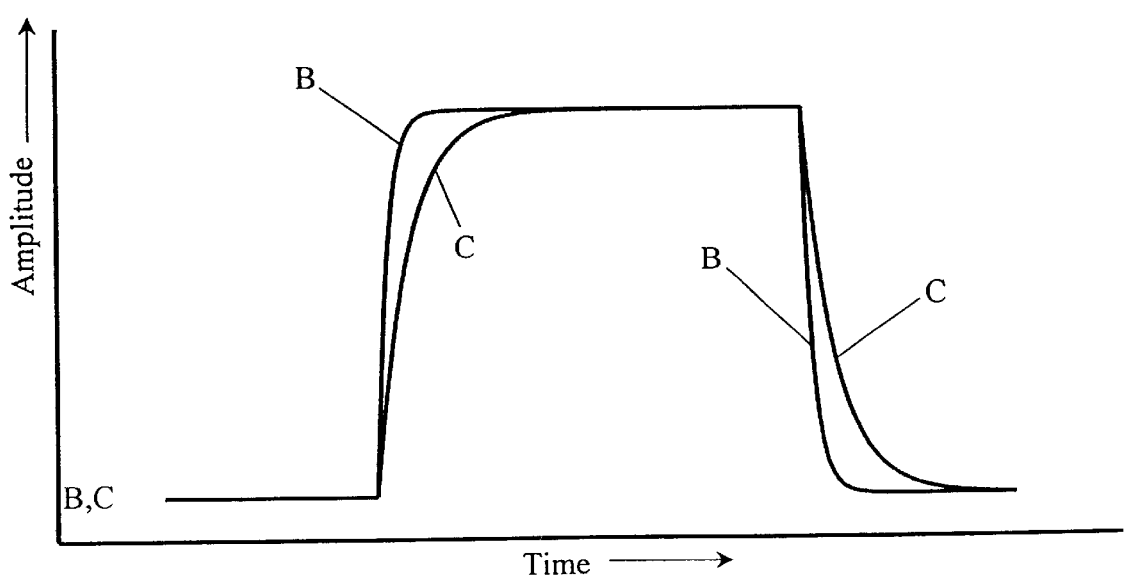
FIG. 4 is a graph comparing waveform B from FIG. 3 and waveform C, which is waveform B after passing through the core and transmission lines 5b, 5, 5a of FIG. 2.

FIG. 4 compares two waveforms B and C. B is the same waveform as in FIG. 2. This waveform is used as the transmitted pulse from the line driver 8 of FIG. 2. After passing through the core and transmission lines 5b, 5, 5a of FIG. 2, the pulse C arriving at the comparator 6 has degraded rise and fall times due to preferential attenuation of the higher frequencies contained in the pulse.

Figure 5:
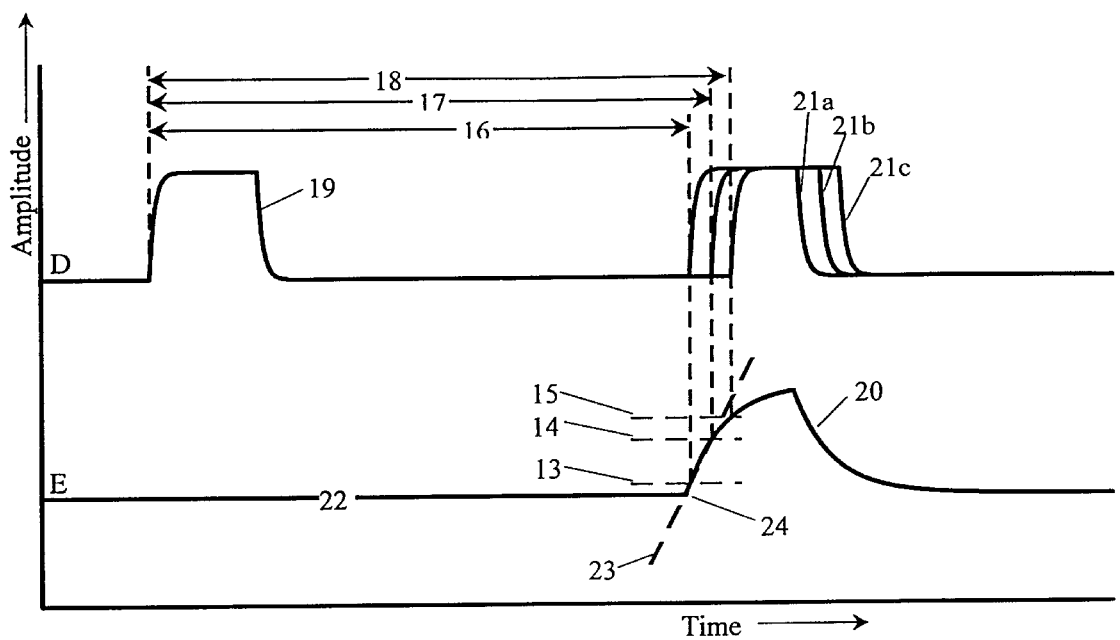
FIG. 5 is a graph showing the timing relationship between a transmitted pulse waveform D and a received pulse waveform E after passage through the apparatus shown in FIG. 2.

FIG. 5 shows the timing relationship between the transmitted pulse waveform D and the received pulse waveform E. The first pulse 19 is generated by the pulse generator 8 at the request of the microprocessor 10. The pulse propagates through the transmission lines and core 5b, 5, and 5a, and arrives at the comparator 6 in a degraded form 20. The comparator 6 triggers the pulse generator 7 to generate a pulse when the level of the received pulse 20 exceeds the level set by the adjustable reference 9. When the reference level is set to 13, pulse 21a is generated. Likewise, when the reference level is set to 14 pulse 21b is generated and when the level is set to 15 pulse 21c is generated. In principle, once a pulse 21a, 21b, or 21c has been generated the sing-around circuit generates an infinite string of pulses having a period of 16, 17, or 18 depending on whether the reference level was set to 13, 14, or 15 respectively, all other things being equal. 22 is the baseline level at which the input to comparator 6 sits when no pulses are being received from the core 6. 24 is the intersection of the rising portion of 20 with the baseline 22. 23 represents the slope of a line tangent to the rising portion of 20 at 24.

Figure 6:
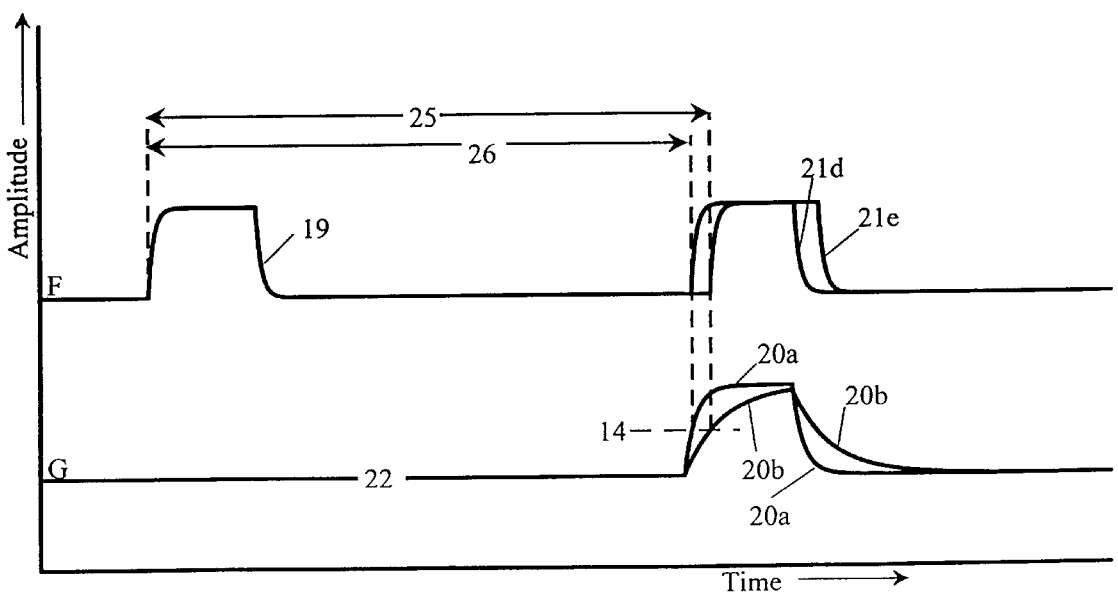
FIG. 6 is a graph showing the effect that variations in the rise time of the pulse received at the comparator 6 of FIG. 2 have on the measured period of oscillation of the sing-around circuit.

FIG. 6 shows the effect that variations in the rise time of the pulse received at the comparator 6 have on the measured period of oscillation of the sing-around circuit. The upper waveform F represents transmitted pulses while the lower waveform G represents received pulses. Received pulse 20a has a fast rise time while received pulse 20b has a slow rise time. With a fixed reference level 14, pulse 20a gives rise to pulse 21d which, together with pulse 19, has a period of oscillation 26. Pulse 20b gives rise to pulse 21e, which, together with pulse 19 has a period of oscillation 25. As can be seen from FIG. 6, the period 26 is smaller that the period 25.

Figure 7:
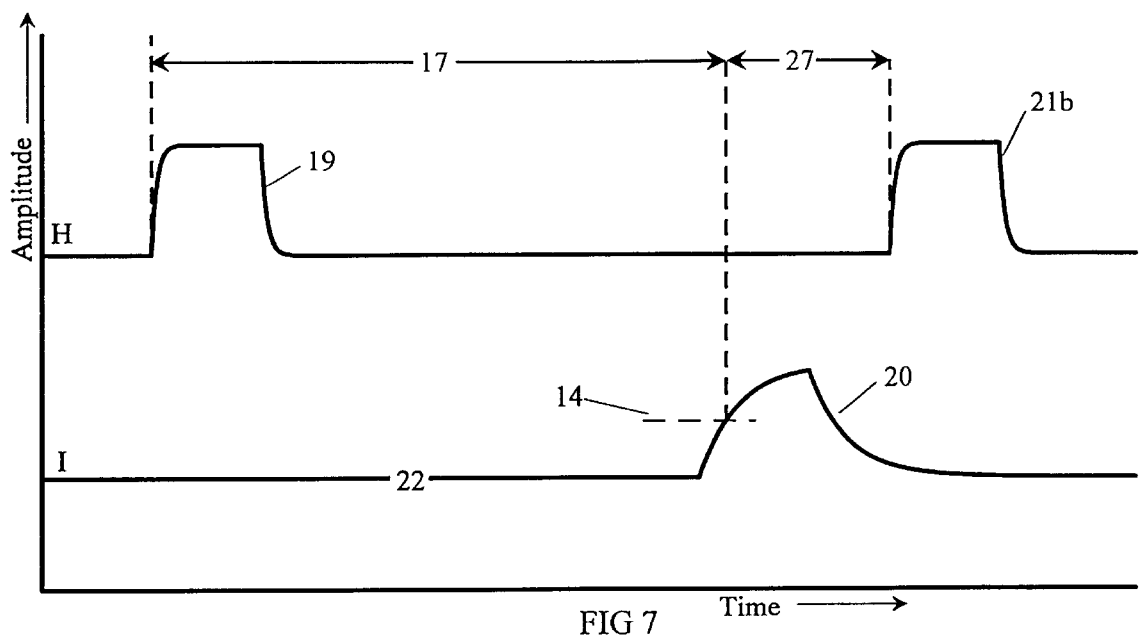
FIG. 7 is a graph showing the additional time 27 added to the period of oscillation 17 due to the non-zero propagation delay through the electronics of FIG. 2.

FIG. 7 shows the additional time 27 added to the period of oscillation 17 due to the non-zero propagation delay through the electronics. The upper waveform H represents transmitted pulses while the lower waveform I represents received pulses.

Figure 8:
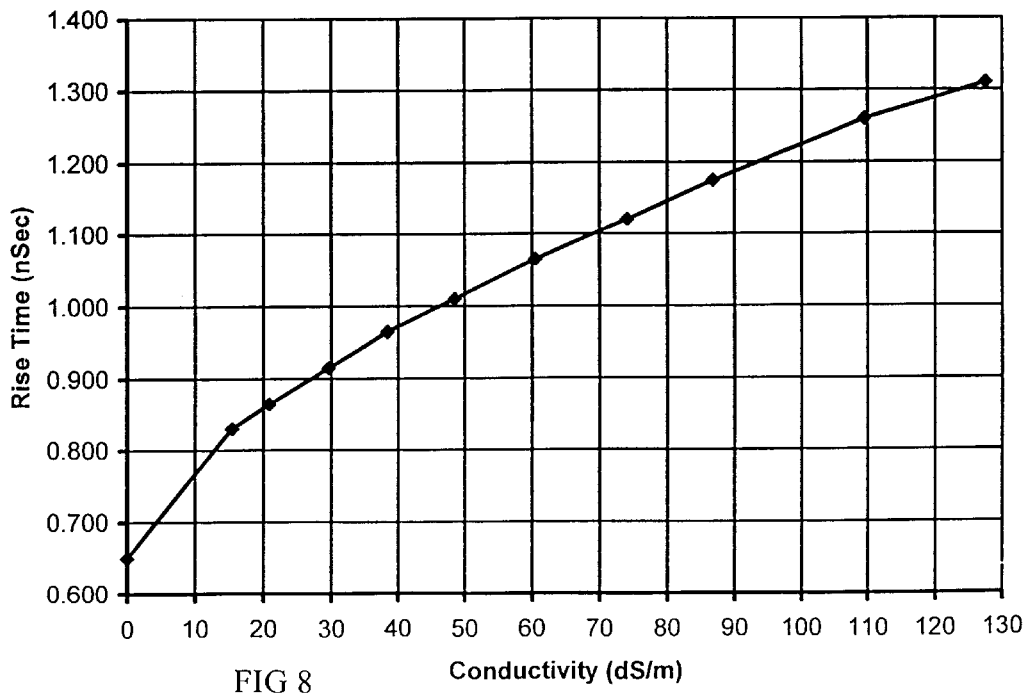
FIG. 8 is a graph showing an empirically determined relationship between the rise time of the pulse received at the comparator 6 and the bulk conductivity of the fluid passing through the core 5 of FIG. 2.

FIG. 8 shows an empirically determined relationship between the rise time of the pulse received at the comparator 6 and the bulk conductivity of the fluid passing through the core 5.

Figure 9:
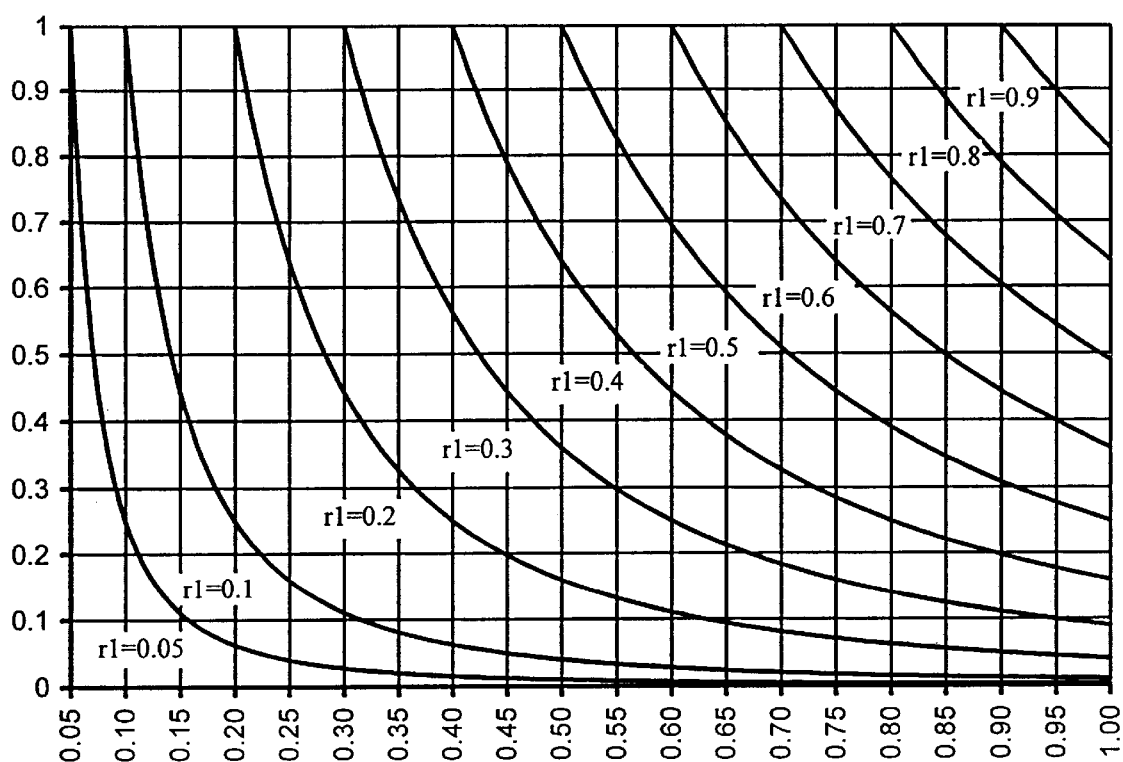
FIG. 9 is a graph displaying the geometrical dependence of the weighting function of a coaxial transmission line.

FIG. 9 displays the geometrical dependence of the weighting function of a coaxial transmission line. The electric field within a coaxial transmission line is not uniform. The field strength is highest at the outer surface of the inner conductor and lowest at the inner surface of the outer conductor. The field strength at a point between the conductors is a non-linear function of the distance of that point from the axis of the coaxial structure. Any fluid passing through the annular gap between the conductors will present an average dielectric constant to the coaxial structure and it is this average dielectric constant that is measured. The contribution to the average dielectric constant that is made by a small portion of that fluid is proportional to the square of the electric field strength experienced by that portion of fluid. Because the electric field strength is position dependent, the portions of fluid closest to the inner conductor contribute more to the average dielectric constant than do the portions of fluid near the outer conductor. To determine the average dielectric constant for the whole annular gap one needs to integrate the contribution of each portion of fluid within the gap, but each portion must be multiplied by a weighting function whose amplitude is determined by the position of that portion of fluid within the gap. FIG. 9 shows the weighting function for ten different geometries of coaxial structures. The inner diameter of the outer conductor is set to 1 in each case. The outer diameter of the inner conductor r1 is varied from 0.05 to 0.9. The weighting function for each case is set to 1 at the position of the outer diameter of the inner conductor. The weighting functions show that as the outer diameter of the inner conductor decreases relative to the inner diameter of the outer conductor, the portions of fluid near the inner conductor start making a disproportionately large contribution to the overall average at the expense of the portions of fluid near the outer conductor. The weighting function is given by Knight, J. H. "The Sensitivity of Time Domain Reflectometry Measurements to Lateral Variations in Soil Water Content", Water Resour. Res. V. 28, 1992 pp 2345–2352.

Figure 10:
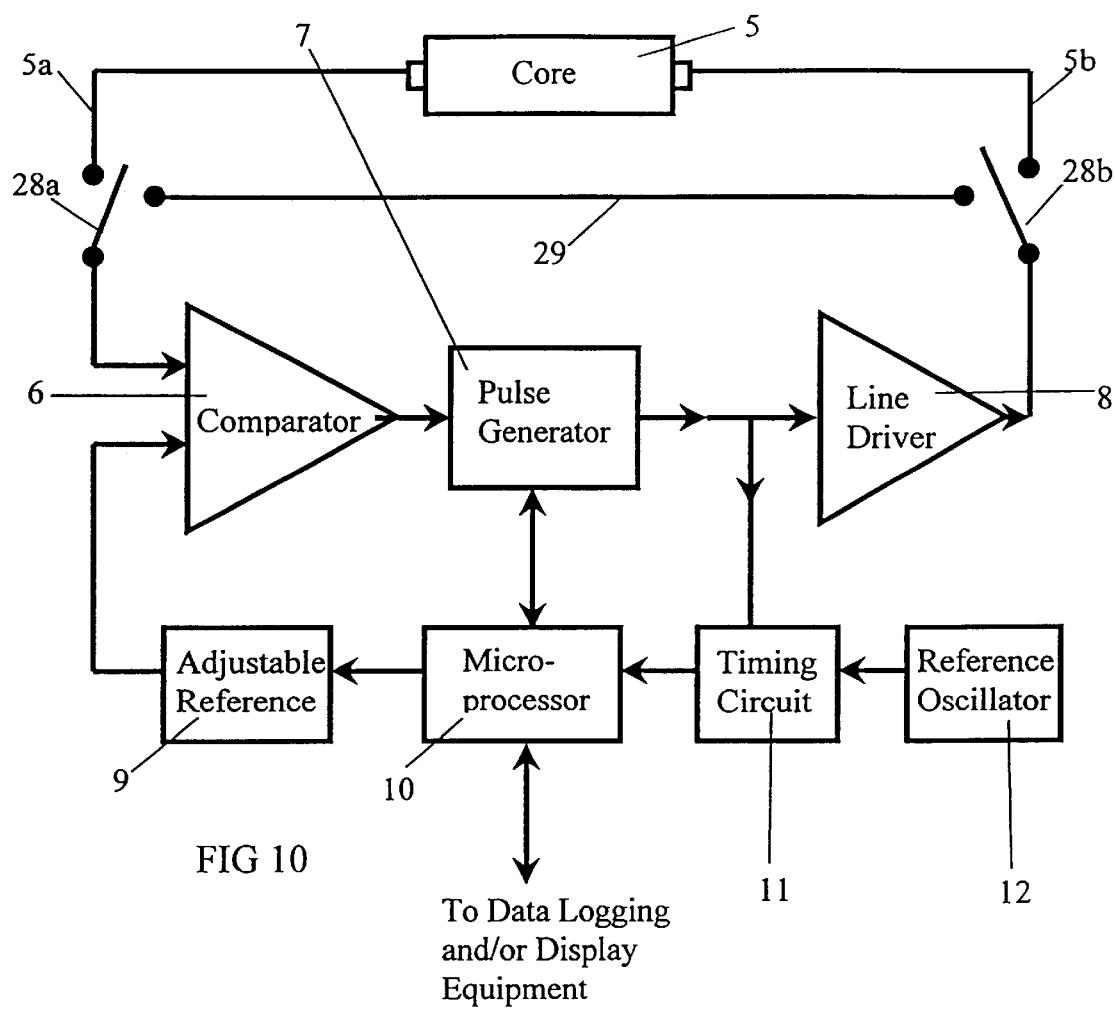
FIG. 10 shows a circuit diagram similar to FIG. 2 except that RF switches 28a and 28b and reference transmission line 29 are added to the system.

FIG. 10 shows a circuit diagram similar to FIG. 2 except that RF switches 28a and 28b and reference transmission line 29 are added to the system. These additions make it possible to compensate the system for variations in the propagation delay time of the electronics.

FIG. 11 shows an alternative electronic circuit that can be used instead of the sing-around circuit. A free running oscillator 31 produces a square wave output that feeds into line drivers 8a and 8b. These line drivers, capable of very fast slew rates, boost the signals and feed them to the core 5 and the reference transmission line 30 respectively. The signals arrive at the comparators 6a and 6b respectively. The level of these signals are compared to the level of the adjustable references 9a and 9b respectively, each of which is controlled by the microprocessor 10. The output of each comparator is fed into an exclusive OR gate 32. The output of the exclusive OR is a series of pulses whose widths are directly related to the dielectric constant of the fluid flowing through the core 5.33 is a circuit that converts pulse width to a base band signal suitable for input to a microprocessor.

FIG. 12 shows the timing relationship of the signals generated in circuit of FIG. 11. J is the output of the free running oscillator. K and L are the outputs of the line drivers 8a and 8b respectively. M is the output of comparator 6a. N is the output of comparator 6b. O is the output of the exclusive OR 32.

Figures 13A, 13B:
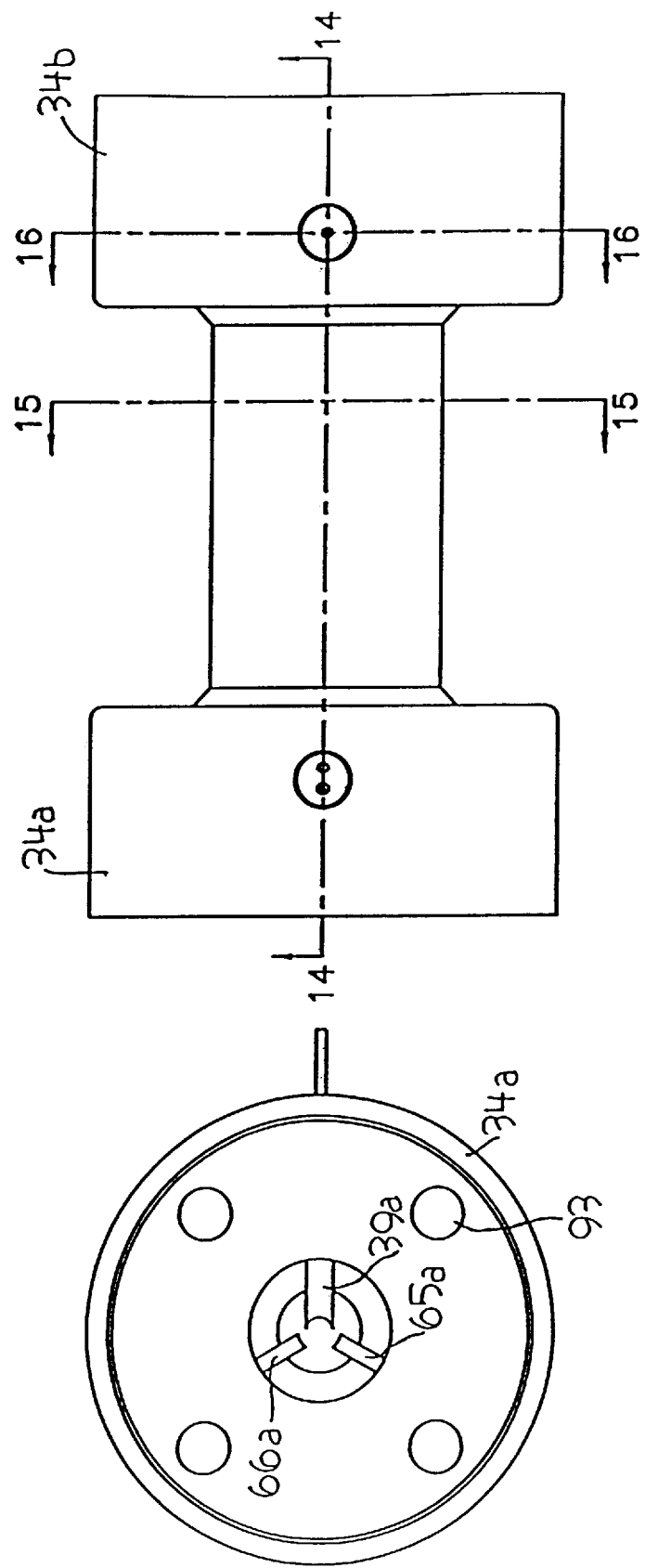
FIGS. 13A and 13B show respectively a plan view and end view of the outside of an embodiment of a device according to the invention.

In FIGS. 13A and 13B respectively shows the plan view and end view of the outside of the device, with flange hubs 34a and 34b, support pylons 39a, 65a, 66a and bolt holes 93 for sandwiching seal plate 43a between the hub 34a and a flange of a pipe through which the fluid to be measured is conducted into and out of the sensor. FIG. 14A and FIG. 14B show cross section 14 of the device with details of the core assemblies and the details of the cable penetrators at each end of the device. The difference between FIG. 14A and FIG. 14B is that FIG. 14A has a thermowell 36, which houses a temperature sensor 37, o-rings 35 that form a pressure tight seal between the thermowell 36 and the penetrator body 44. FIG. 14B does not have these items. Furthermore, the penetrator body 44 and o-ring retaining plate 47 shown in FIG. 14A are slightly different that penetrator body 58 and o-ring retaining plate 62 shown in FIG. 14B in order to accommodate the presence of the thermowell 36. Aside from these differences, FIG. 14A and FIG. 14B are mirror images of each other. Therefore, only FIG. 14A will be described. FIG. 14A shows the flange hub 34a, seal plate 43a These two parts together provide a means of connecting the device into a piping system via a standard ANSI 150 four-bolt raised face flange. The flange hub 34a is welded to a pressure pipe 49. Suspended within the pressure pipe 49 is the core assembly consisting of the inner conductor 57, which is received within spider body 51a, from which extends spider leg 50a, with washer 53a, insert 56a, and o-ring 52a between the spider body 51a and the inner conductor 57. Also, in the core assembly are SMA center contact pin 54a which connects to the inner conductor of cable 38a, threaded plug 55a, and outer conductor 48. A commercially available semi-rigid cable 38a is connected to the core assembly via a commercially available right angle SMA connector 41a. The inner and outer conductors of the cable 38a form feed lines for the conductors 57 and 48. The semi-rigid cable 38a passes through a penetrator body 44 to the low pressure side of the penetrator. The o-rings 46 form a pressure tight seal between the semi-rigid cable 38a and the penetrator body 44. The o-ring retaining plate 47 keeps the o-rings 35 and 46 from falling out of place during manufacture of the device. The o-rings 45 form a pressure tight seal between the penetrator body 44 and the flange hub 34a. The thermowell 36, semi-rigid cable 38a, and core assembly are encapsulated in a moldable resin 40. The resin is molded to form three support pylons 39a, 65a, 66a and an annular gap 63. The pylons provide mechanical support and protection from abrasion for the core assembly. Pylon 39a also provides mechanical support and protection from abrasion for the semi-rigid cable 38a. The resin also forms a thick uniform layer over the outside of the inner conductor 57 and the inside of the outer conductor 48.

The pressure vessel consists of two flange hubs 34a and 34b welded to each end of a pressure pipe 49. In the end of each flange hub is a seal plate 43a and 43b. Each flange hub, in combination with its respective seal plate forms an interface that mates with a standard 4-bolt ANSI 150 raised face flange. The purpose of the seal plate is two-fold, to provide a surface for the raised face flange to bear upon and to provide an o-ring seal.

The electrode core consists of an inner conductor 57, and an outer conductor 48. Each conductor is suspended inside the pressure pipe 49 by a spider assembly at each end. The inner conductor 57 consists of a solid metal bar. However, any arrangement that provides a conducting surface at the same radius as outside diameter of the metal bar is sufficient. Likewise, the outer conductor 48 consists of a thin wall metal cylinder, however, any arrangement that provides a conducting surface at the same radius as the inside diameter of the outer conductor is sufficient.

The preferred embodiment of the inner conductor has a thin coating covering the inner conductor in addition to a moldable resin encapsulation 40. The thin coating provides DC electrical isolation between the inner conductor 57 and the outer conductor 48 and between the inner conductor 57 and the pressure pipe 49 and flange hubs 34a and 34b. This DC isolation prevents the loading of the driver circuit 8 when the bulk conductivity of the fluid being measured increases. There are a number of coatings available that will perform this task. The preferred embodiment uses a spray on epoxy coating. The moldable resin encapsulation 40 displaces the fluid being measured from the area of high sensitivity. This has advantages as described below. The preferred embodiment uses a urethane potting resin, however, other moldable materials such as Teflon, would be suitable. Because the DC isolation and the displacement of fluid from the high sensitivity area are separate functions it is advantageous to separate devices to accomplish these functions. Coatings that provide good DC isolation are not normally available in large thicknesses and coatings that are available in large thicknesses have been found to be poor DC isolators under the flow and pressure conditions normally found in oil pipelines. Therefore, the use of two separate devices allows the selection of the thin coating to be optimized for DC isolation and the selection of the moldable resin to be optimized for structural strength and wear resistance.

Each spider assembly contains a spider body 51a and 51b, washer 53a and 53b, insert 56a and 56b, sealing o-ring 52a and 52b, spider leg 50a and 50b, threaded plug 55a and 55b, and SMA center contact pin 54a and 54b. The spider bodies and spider legs are made from 316 stainless steel. The spider legs 55a and 50b are spaced uniformly around the core to distribute the electrical transient to the outer conductor through the three connections formed by the spider legs 50a and 50b. In this example, there are three connections 50a and three connections 50b, which has been found suitable for a device in which the inner radius of the outer conductor 48 is about 1.25 inches, the outer radius of the inner conductor 57 is about 0.5 inches and the length of the inner and outer conductors is about 18 inches. For smaller devices, a device having two connections is believed to be an improvement over a device with only one connection. For larger devices, it is believed desirable to include additional connection points. The object is to suppress higher order modes by providing uniformly distributed feeds to the outer conductor.

The material forming the spider legs was chosen for strength and corrosion resistance. The washer and insert need to be made from a material whose dielectric constant is stable under all operating conditions. The preferred embodiment uses Teflon™ for these parts, but other suitable materials are available such as Delrin™. The SMA center contact pin is a gold plated brass part that is available from SMA connector manufacturers. This contact is the same contact pin that the connector manufacturer uses in fabricating commercial female SMA connectors. The threaded plug is a brass part into which the SMA center contact is soldered. The contact/plug assembly is screwed into the end of the inner conductor. The thin coating of the inner conductor does not extend to the threads machined into the end of the inner conductor so the contact/plug assembly makes electrical contact when it is screwed into the inner conductor. When the insert is inserted into the spider body and the spider body and insert are placed over the contact/plug assembly this group of parts presents a female SMA connector to mate with the male right angle SMA connector 41a or 41b. The end of the inner conductor and the inside diameter of the spider body have grooves machined into them that are intended to provide a seat for the o-ring 52a. While the o-ring is seated in these grooves it experiences a slight compression from the spider body and the inner conductor. The washer and insert provides a means of completely restricting movement of the o-ring. The thin coating of the inner conductor extends past the o-ring groove, toward the contact/plug assembly. If the spider assembly and inner conductor are exposed to conductive fluid, the compressed o-ring prevents the fluid from reaching either the uncoated portion of the inner conductor or the contact/plug assembly. This, in turn, facilitates an RF connection to the right angle SMA connector while at the same time maintaining the DC electrical isolation of the inner conductor under expected flow and pressure conditions. The corners of the spider body closest to the inner conductor have a generous radius applied to them to minimize the concentration of the electric field at those points. The corners of the inner conductor closest to the spider body have a generous radius applied to them for the same reason. The radiussed corners of the inner conductor also allow the application of a spray on coating of uniform thickness. The presence of corners allows surface tension to cause the spray on coating to aggregate around the corners while the coating is still in its liquid state.

The conductors 48 and 57, spider assemblies, SMA connectors 41a and 41b, and the portion of each semi-rigid cable 38a and 38b on the high-pressure side of the penetrators, are all encapsulated in a urethane resin 40. The urethane is molded in such a manner so as to form a set of three support pylons at each end of the core 39a, 65a, and 66a shown in FIGS. 15 and 39b, 65b, and 66b shown in FIG. 16. Each set of three support pylons at each end of the core has one large pylon and two smaller pylons. Each pylon encapsulates a spider leg running from the spider body to the outer conductor. Additionally, the large pylon at each end of the core encapsulates the semi-rigid cable at each end of the core. Additionally, a pylon at one end of the core encapsulates the thermowell. The encapsulating pylons provide mechanical reinforcement to the spider legs and semi-rigid cable and mechanical support for the inner conductor. Additionally, the pylons protect these elements from abrasion by the fluid being measured. Between each set of pylons the urethane is molded to form an annular gap 63 between the inner and outer conductors. The annular gap is molded in such a way as to create a thick dielectric coating over the inner conductor and inside the outer conductor. The advantages of these thick dielectric coatings are described below. Also, the urethane resin is molded into conical sections at either end of the core to streamline the flow of the fluid past the core. The fluid mixture to be measured flows in one end of the device, around the pylons at one end, along the annular gap completely filling the gap, around the pylons at the other end, and out of the instrument.

The length of the conductors 48 and 57 may be varied to provide a method of improving measurement resolution. The longer the conductors, the greater the resolution of measurement of the dielectric constant of the fluid. There are limits as to how long the conductors can be, however. First, the longer the conductors are, the longer the pressure pipe 49 has to be. This increases the overall weight of the device and makes it more difficult to accommodate in existing piping systems. Second, the longer the conductors are, the greater the attenuation of the pulse that is transmitted through the core. Eventually, the core will reach a length at which the attenuation is so great that the pulse received at the comparator 6 is indistinguishable from noise.

Figure 15:
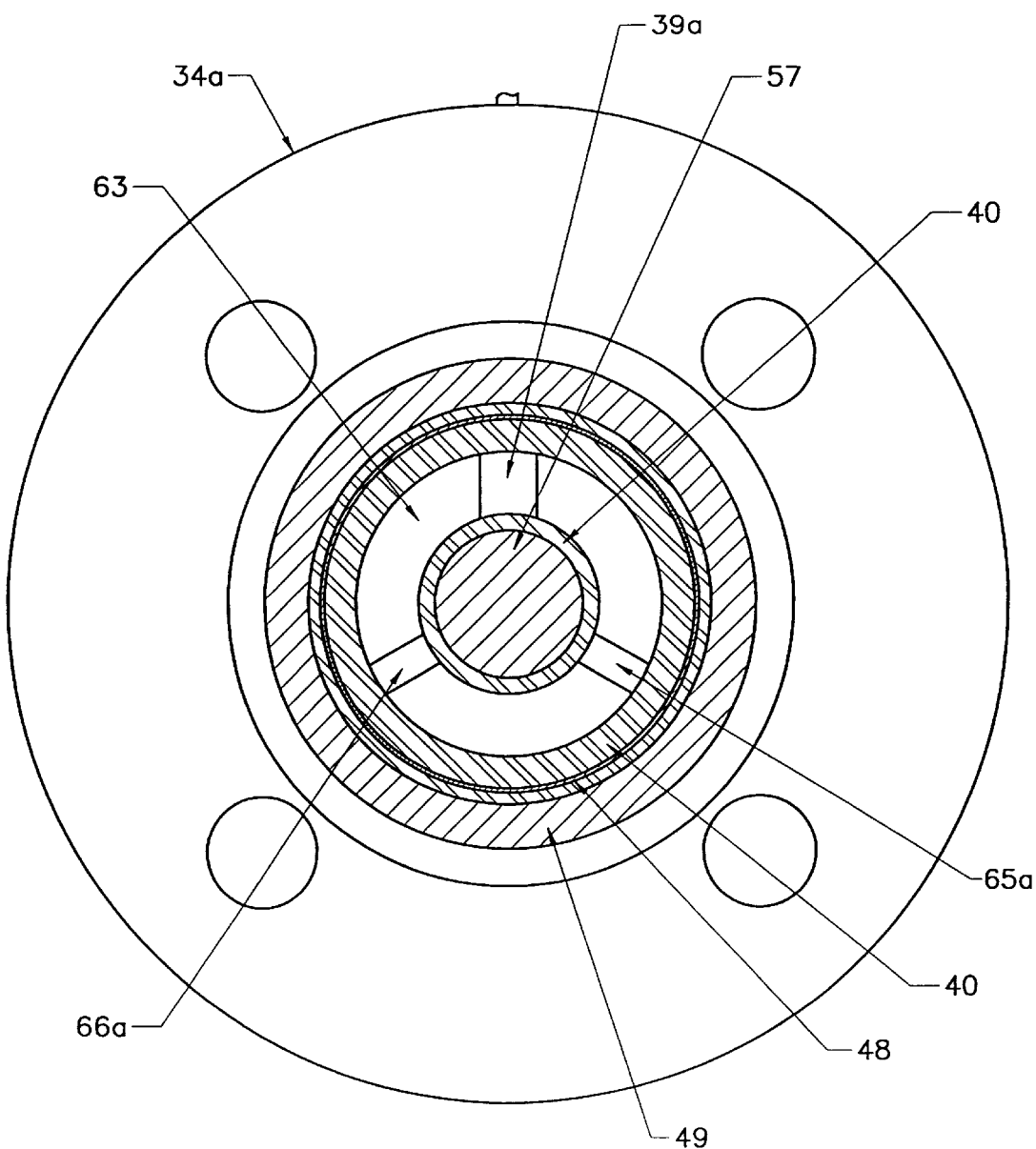
FIG. 15 shows a cross section 15 of an embodiment of the invention.

FIG. 15 shows cross section 15 of the device showing the inner conductor 57, outer conductor 48, support pylons 39a, 65a, and 66a, the flange hub 34a, annular gap 63, and thick resin coating 40 over the inner conductor 57 and the outer conductor 48.

Figure 16:
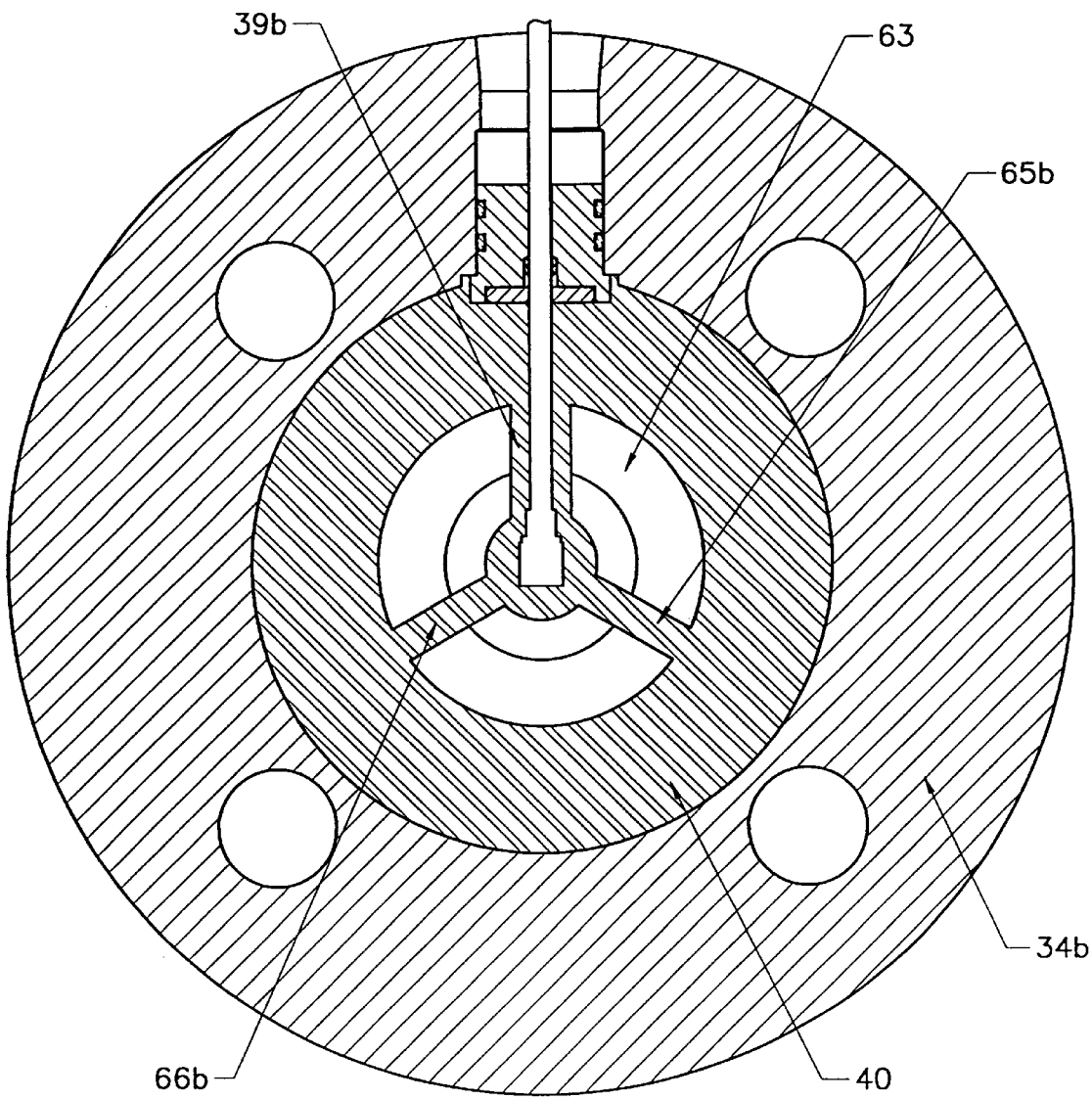
FIG. 16 shows a cross section 16 of an embodiment of the invention.

FIG. 16 shows cross section 16 of the device showing a cross section of the flange hub 34b, a cross section of the support pylons 39b, 65b, and 66b, a cross section of the resin molding 40, and the annular gap 63.

FIGS. 17A and 17B show respectively a plan and end view of the outside of an alternate device configuration which utilizes a parallel transmission line. FIG. 18A and FIG. 18B together show cross section 18 of the alternate configuration of the device. The details of the penetrators, semi-rigid cable, flange hub, seal plate, thermowell, and the mirror symmetry are the same as FIG. 14A and FIG. 14B. FIG. 18A shows the moldable resin 67, creating a conical transition section 68a and a cylindrical fluid conduit 69. The resin encapsulates the alternate spider assembly which includes the outer transition body 70a, alternate insert 72a, alternate washer 75a, SMA center contact 71a, threaded plug 73a, alternate o-ring 76a, and inner transition body 74a.

FIG. 19 shows cross section 19 of the alternate configuration of the device showing the molding resin 67, the fluid conduit 69, and both conductors of the parallel conductor transmission line 77a and 77b.

Figure 20:
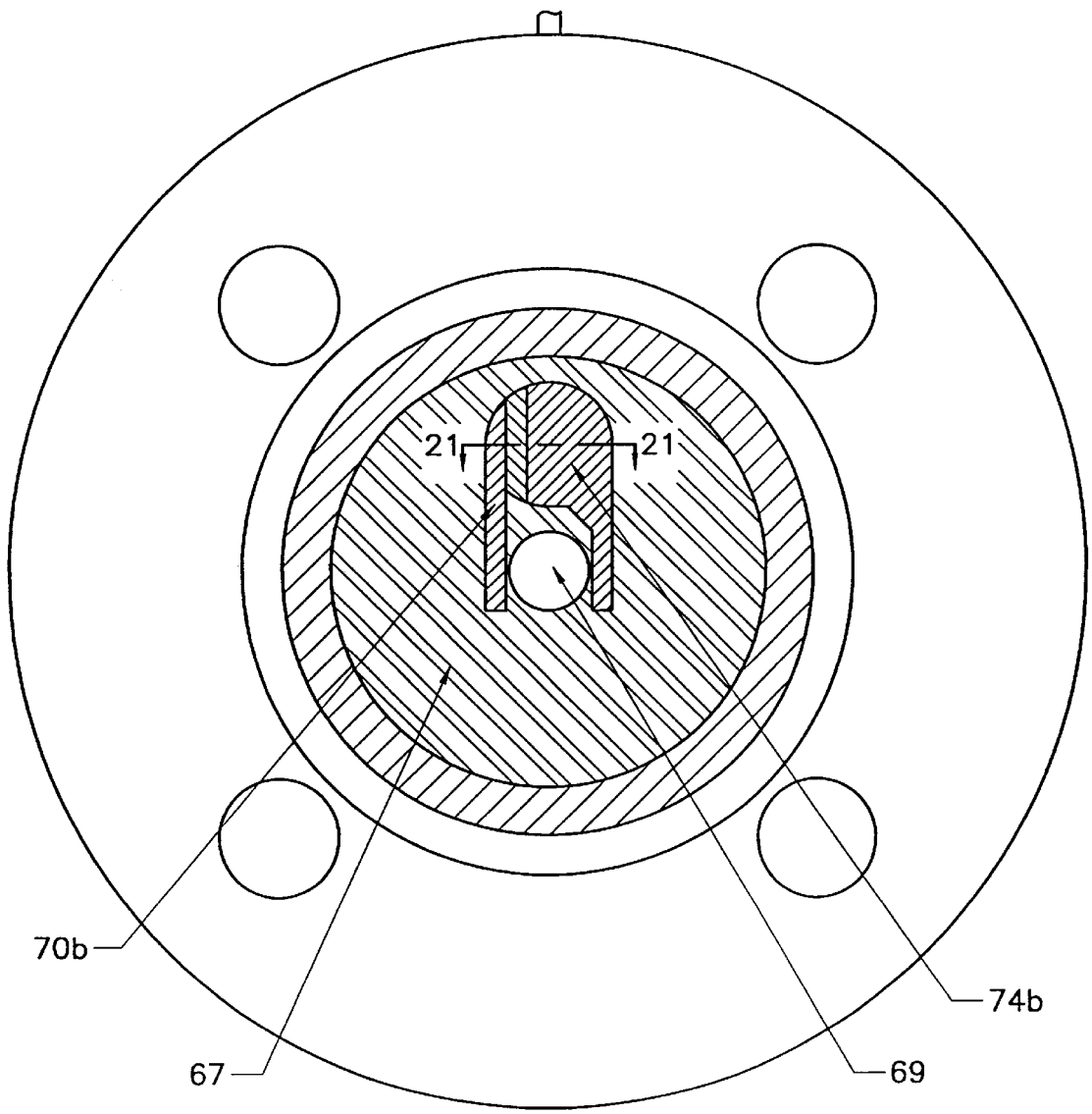
FIG. 20 shows a cross section 20 of the embodiment of FIG. 19.

FIG. 20 shows cross section 20 of the alternate configuration of the device showing the outer transition body 70b and the inner transition body 74b.

Figure 21:
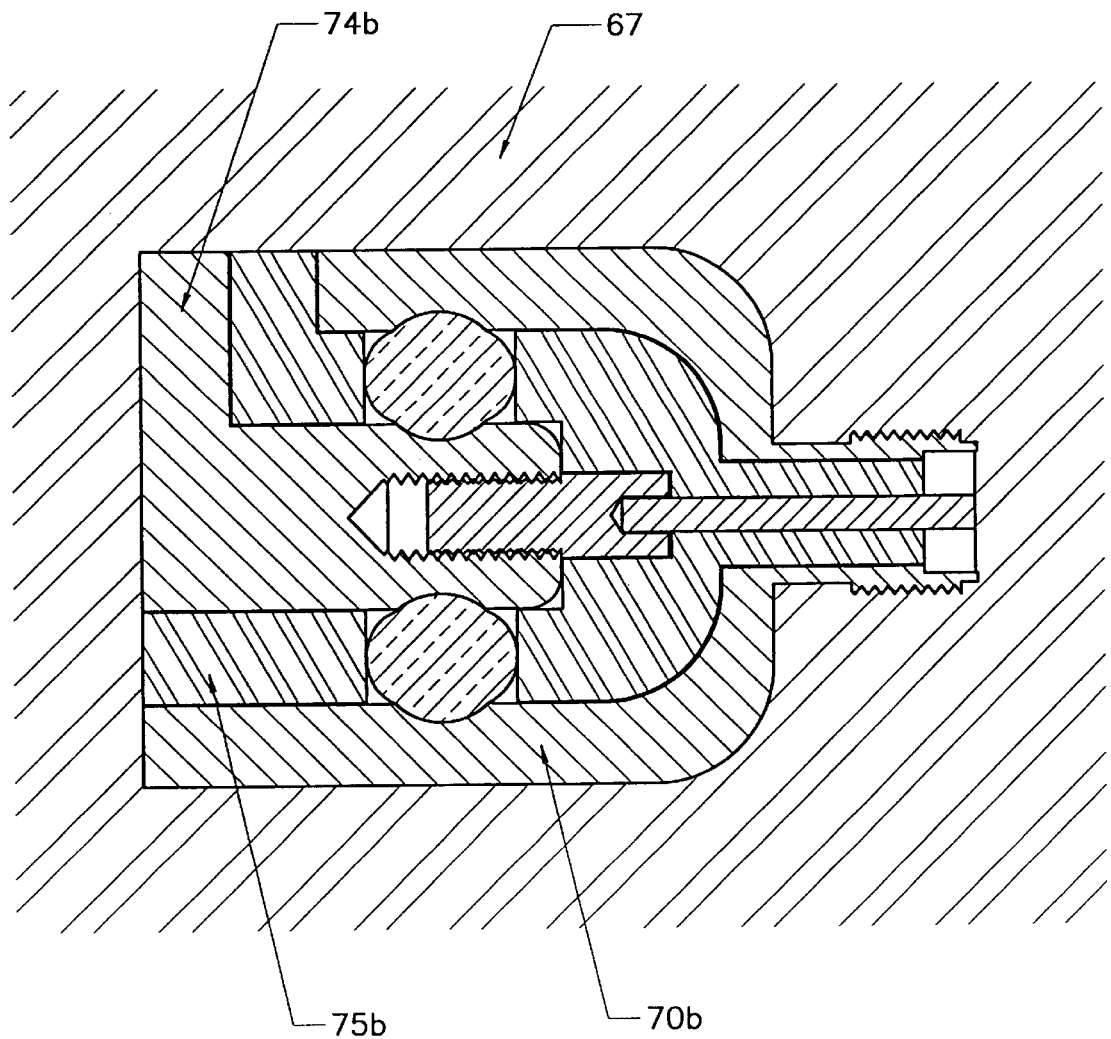
FIG. 21 shows a cross section 21 of the embodiment of FIG. 19.
Figure 22:
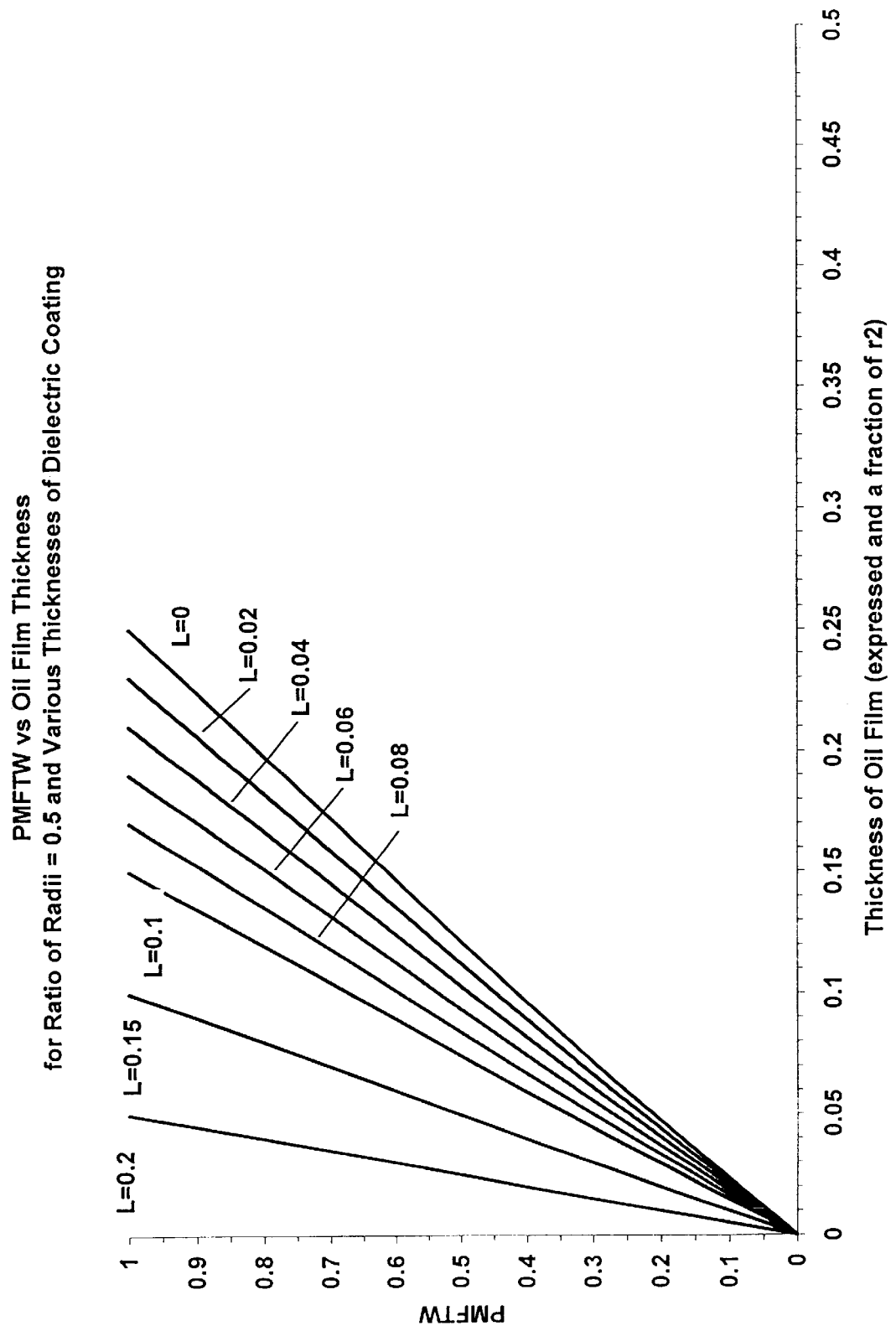
FIG. 22 through FIG. 28 show a sequence of a family of curves depicting the relationship between oil layer thickness, dielectric coating thickness, and signal weighting. For each figure the ratio of radii is fixed. Each curve depicts the relationship between the PMFTW, the portion of maximum fraction of total weighting, and the thickness of the oil layer, for a given thickness of dielectric coating.
Figure 23:
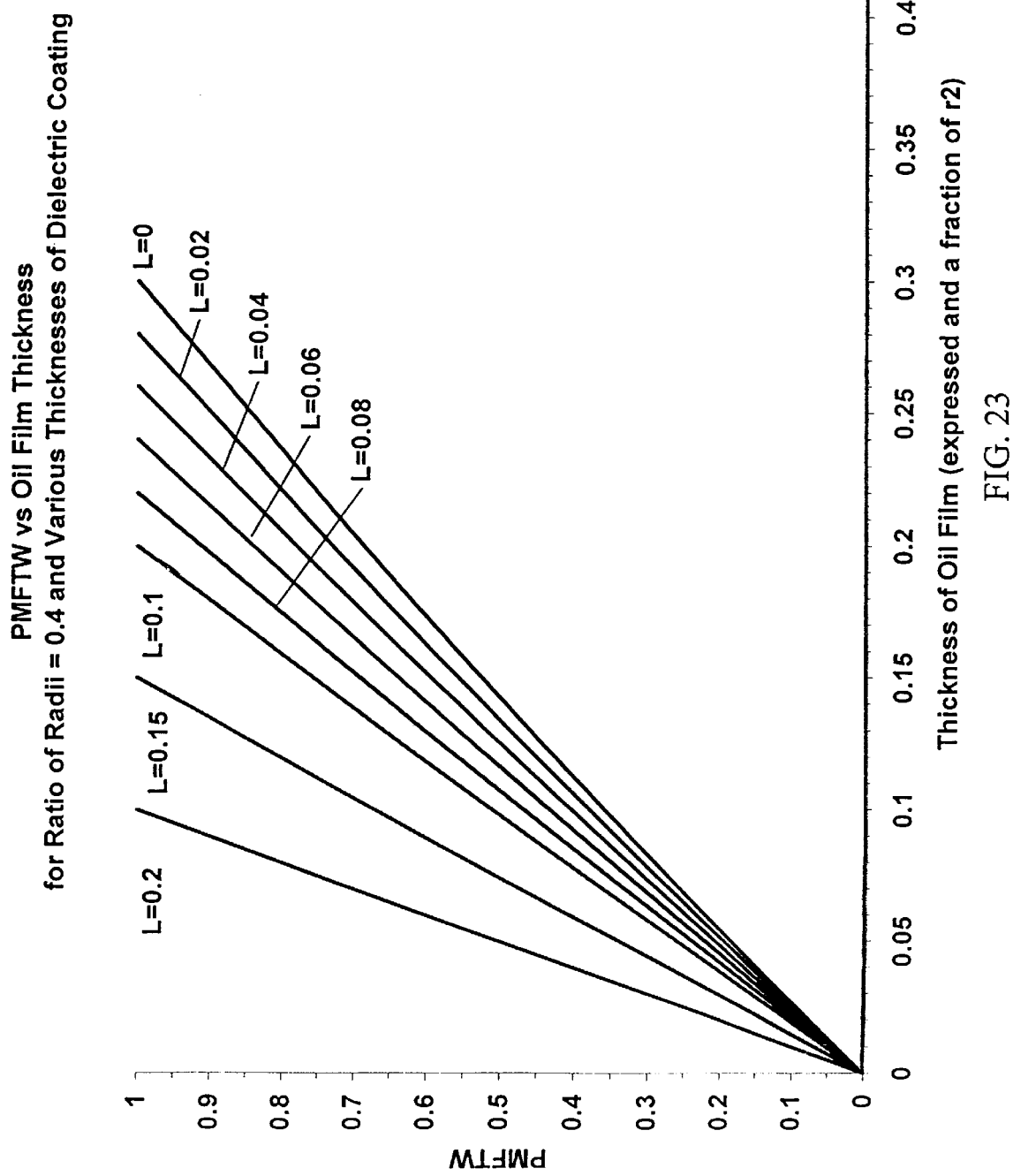
Figure 24:
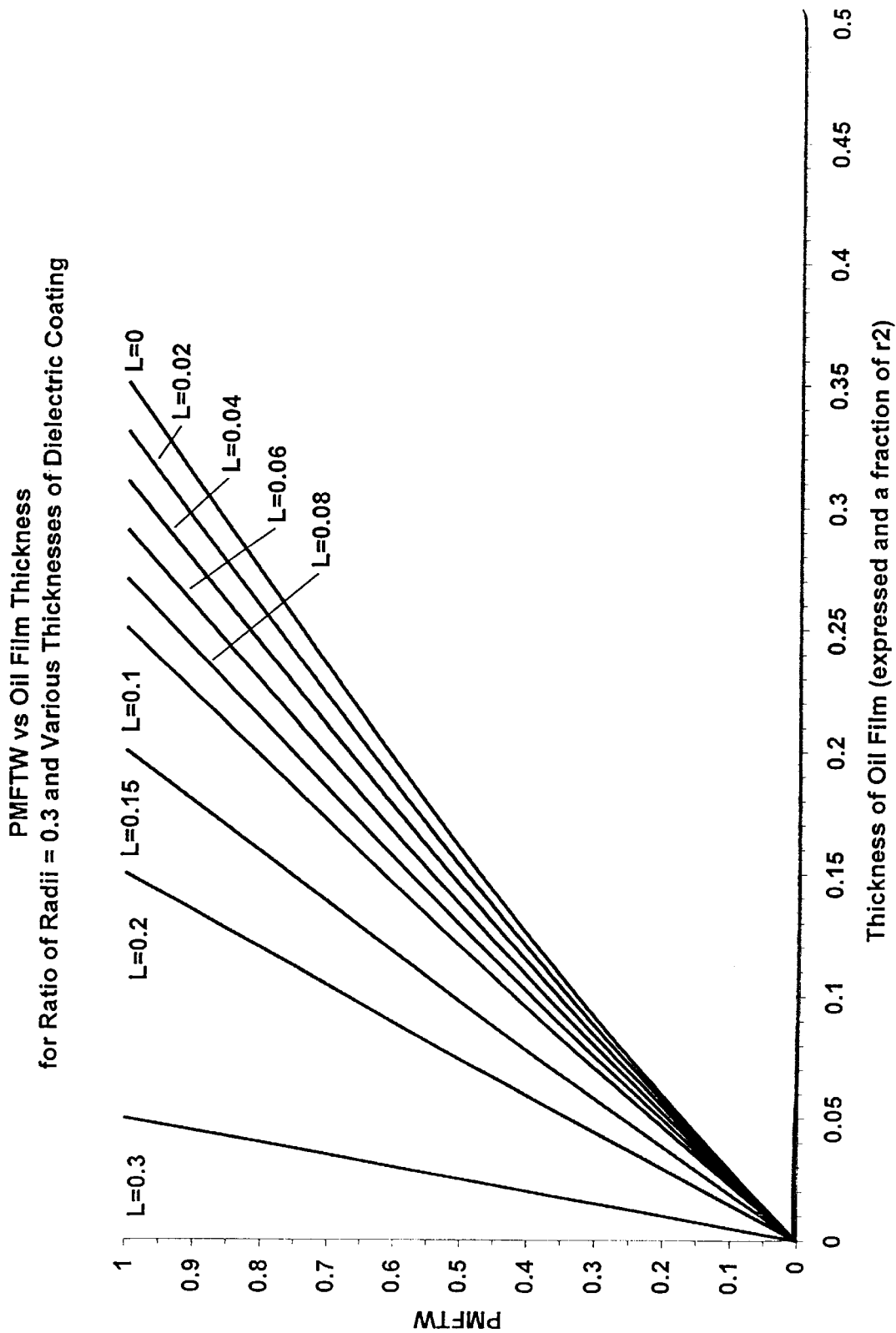
Figure 25:
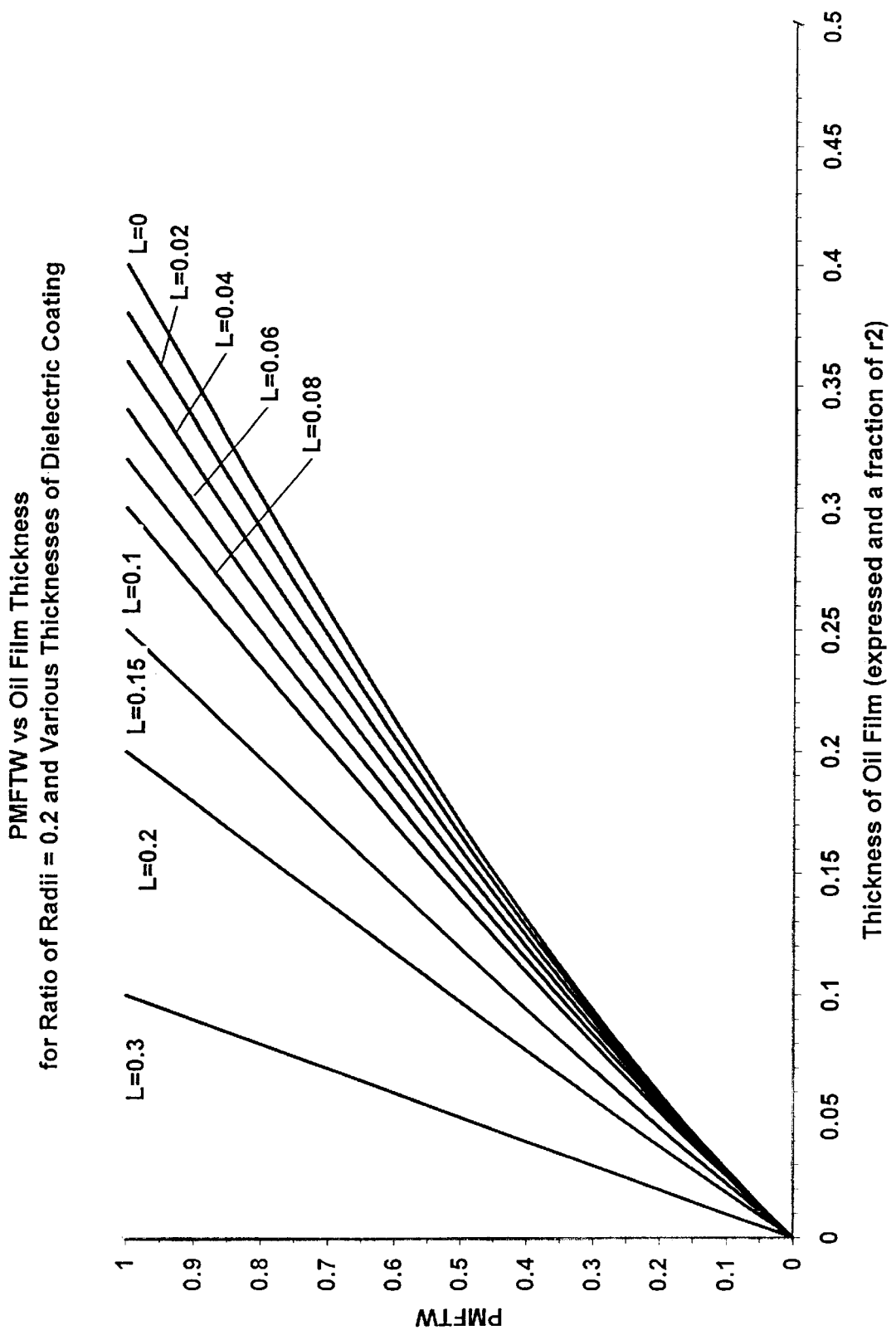
Figure 26:
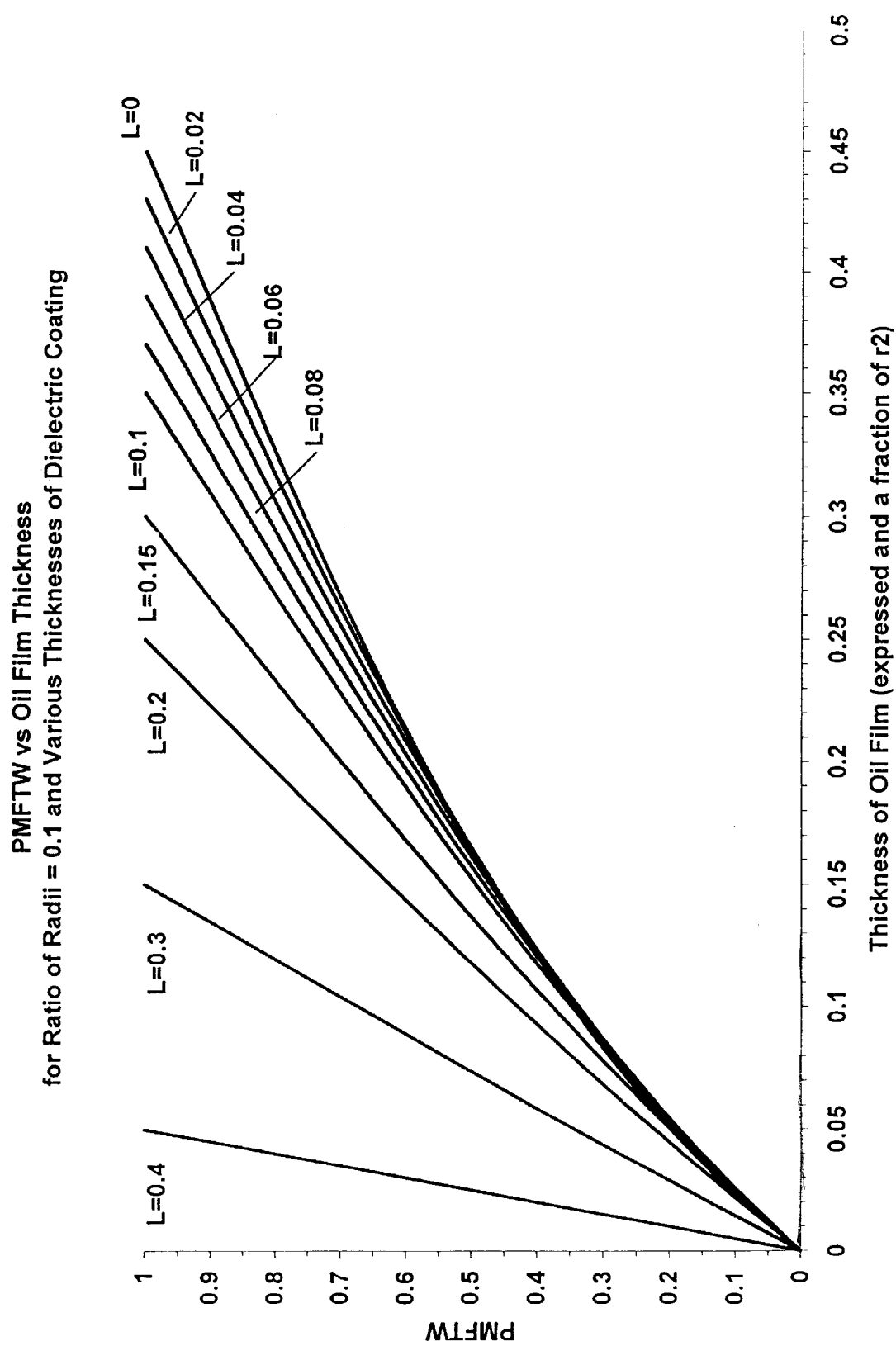
Figure 27:
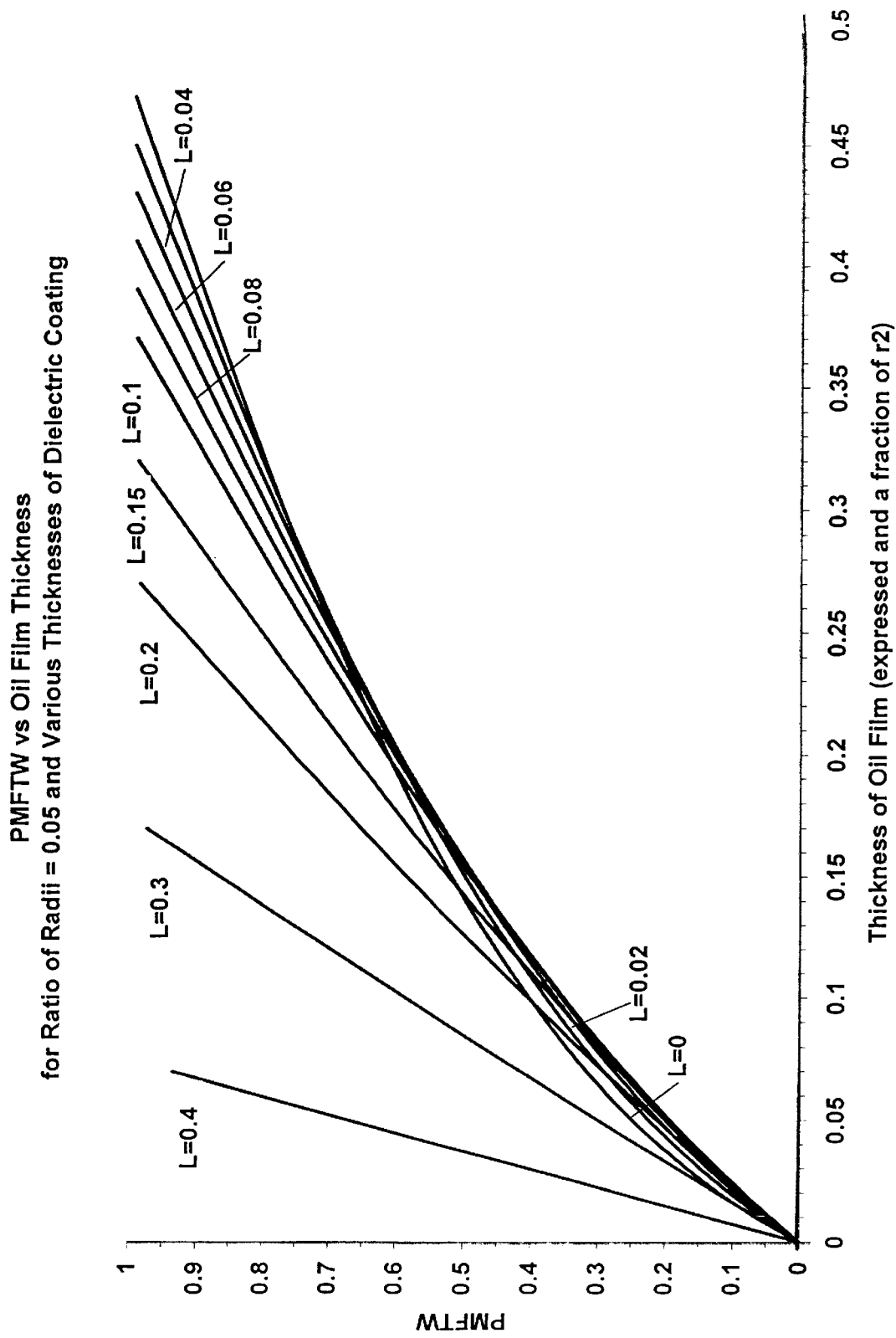
Figure 28:
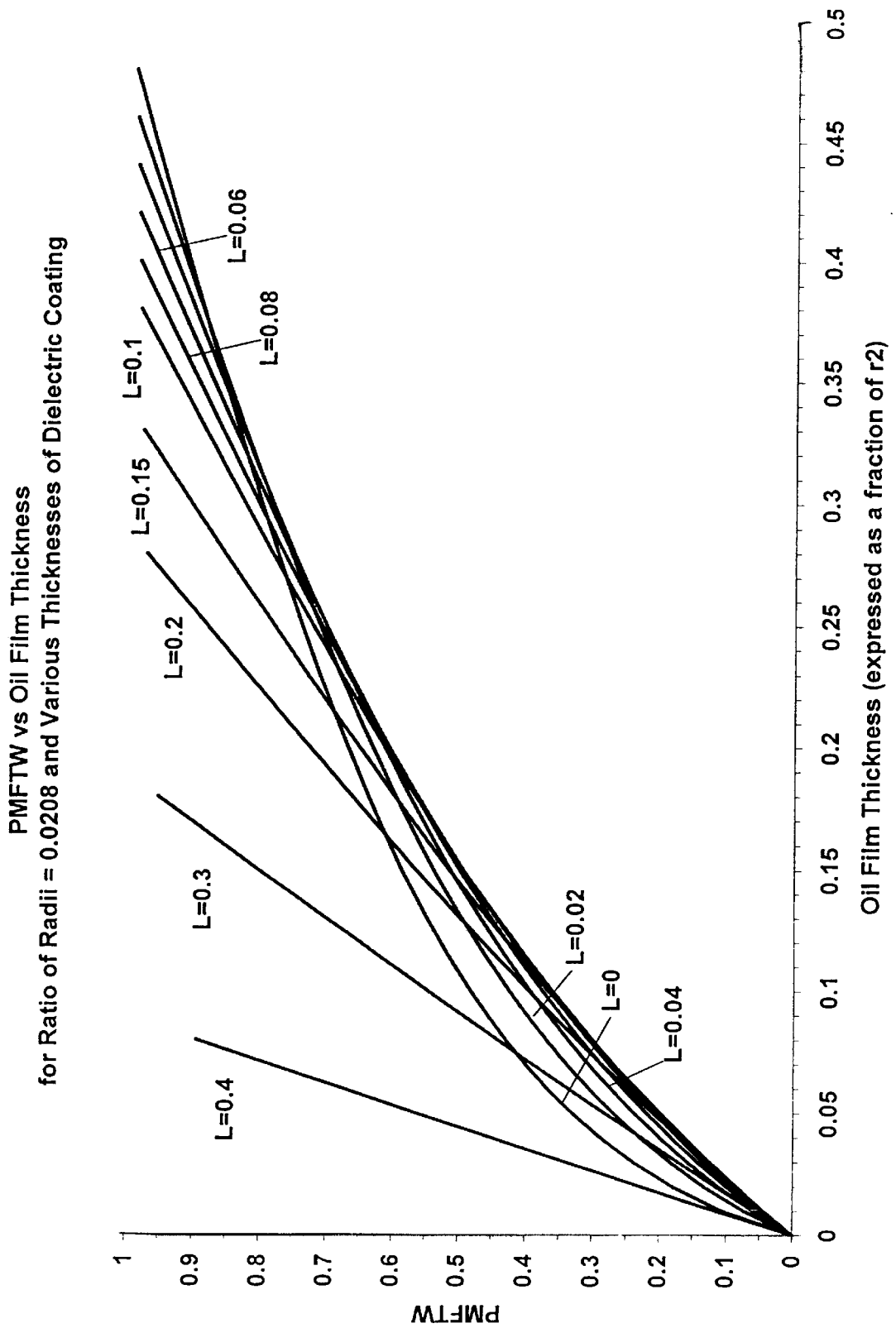
Figure 29:
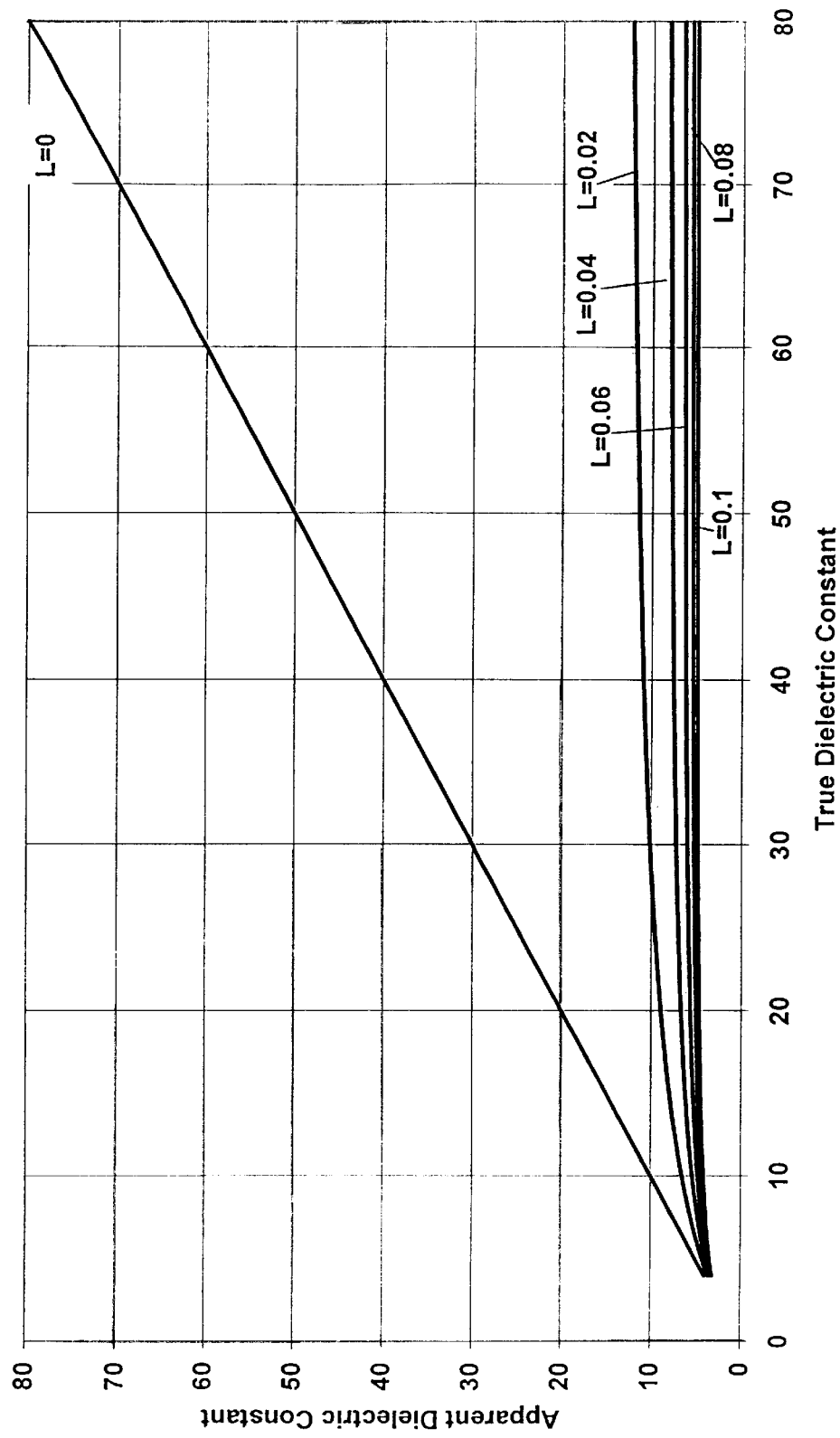
FIG. 29 through FIG. 35 show a sequence of a family of curves depicting the relationship between apparent dielectric constant and the true dielectric constant for various values of ratio of radii and dielectric coating thickness. The ratio of radii is fixed for each figure. Each curve represents the relationship between the apparent dielectric constant and the true dielectric constant for a given thickness of dielectric coating.
Figure 30:
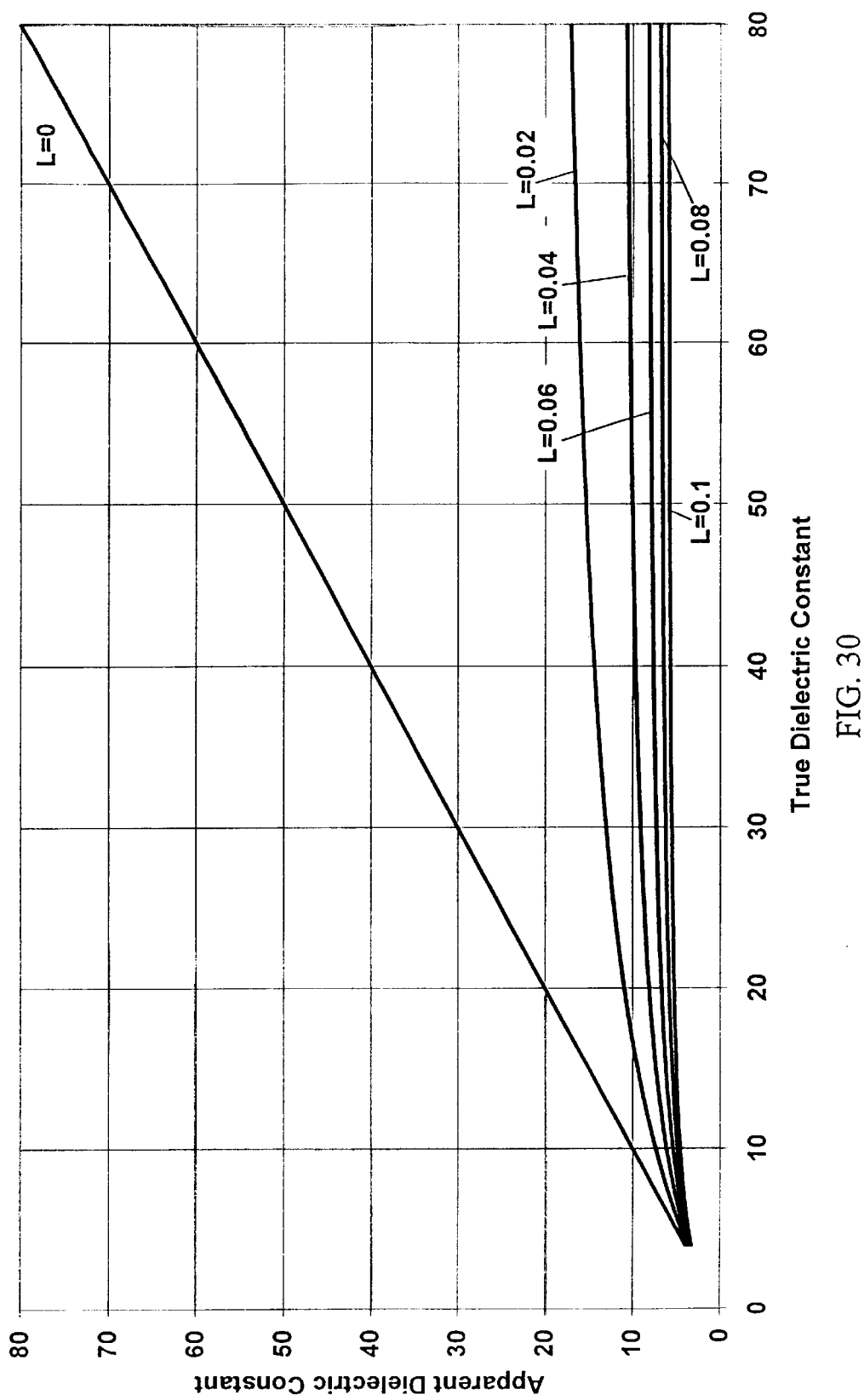
Figure 31:
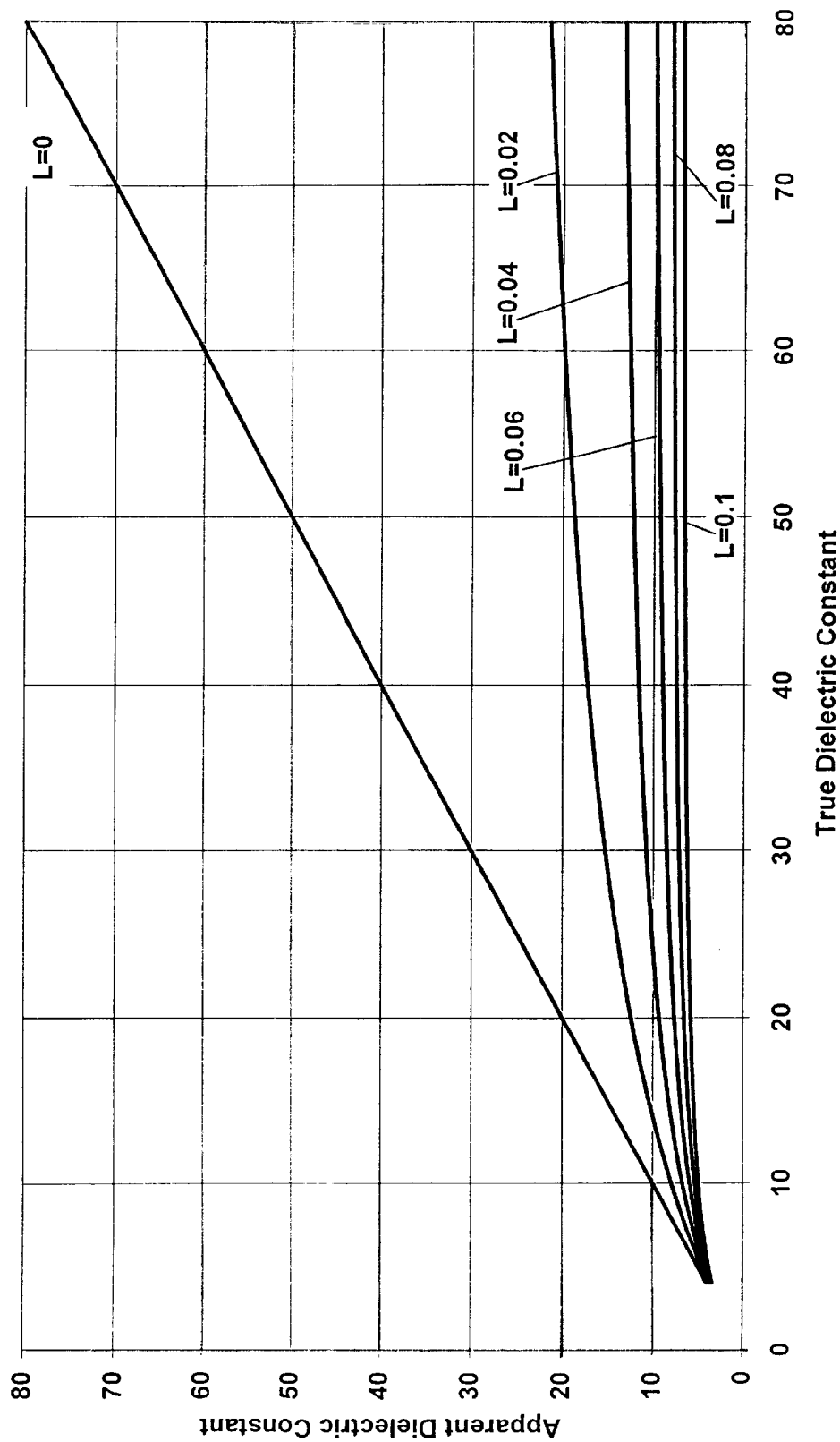
Figure 32:
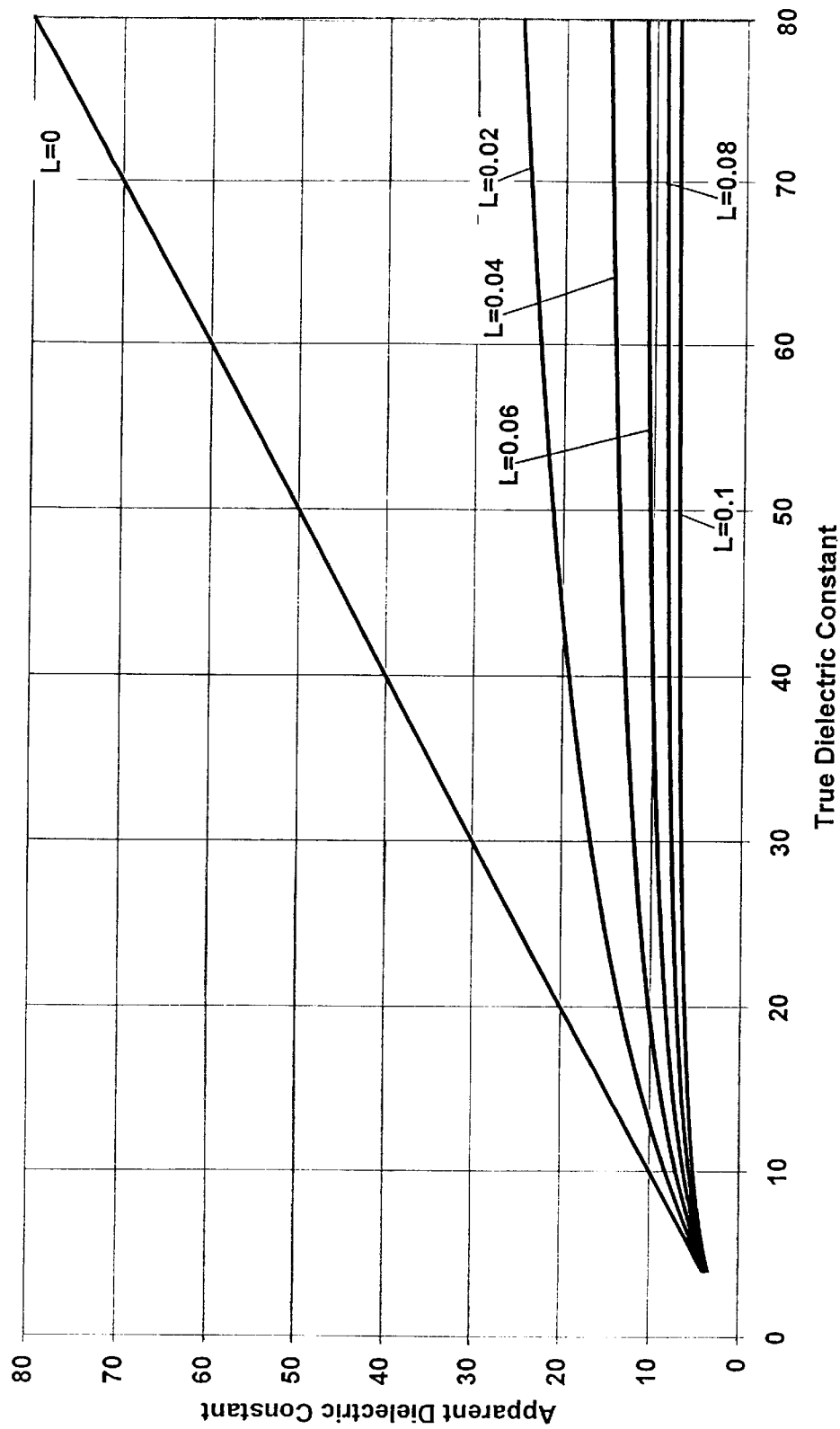
Figure 33:
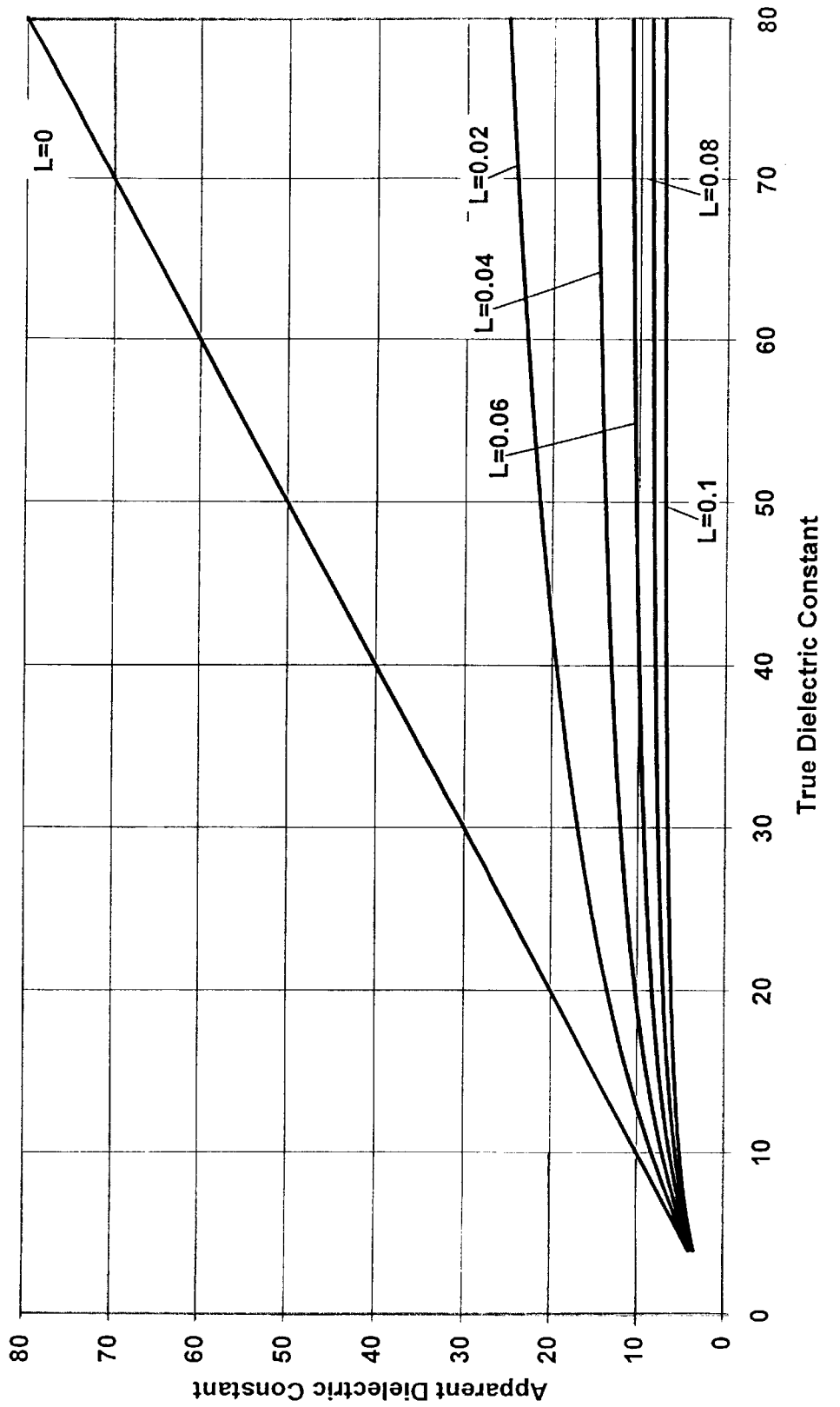
Figure 34:
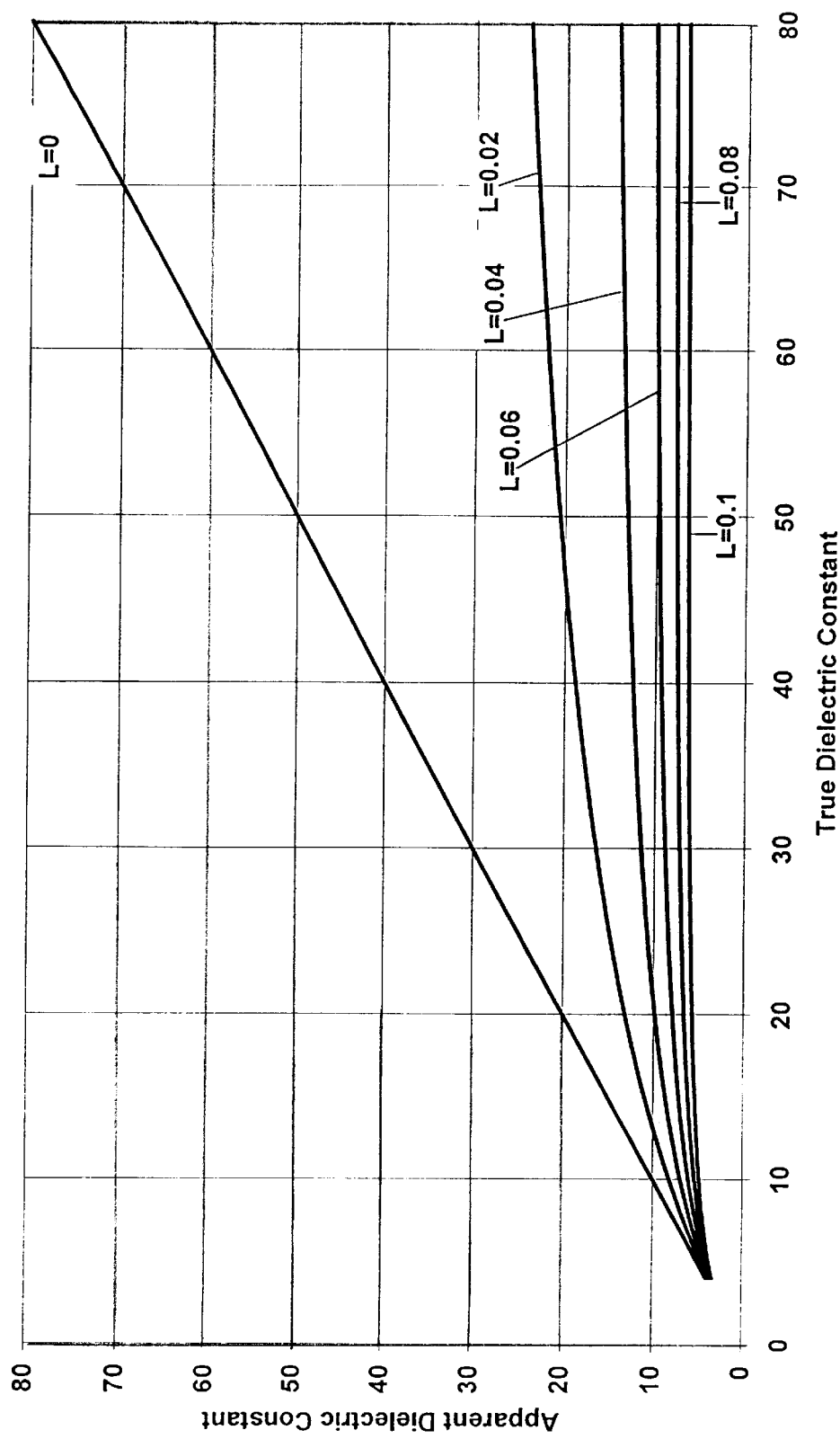
Figure 35:
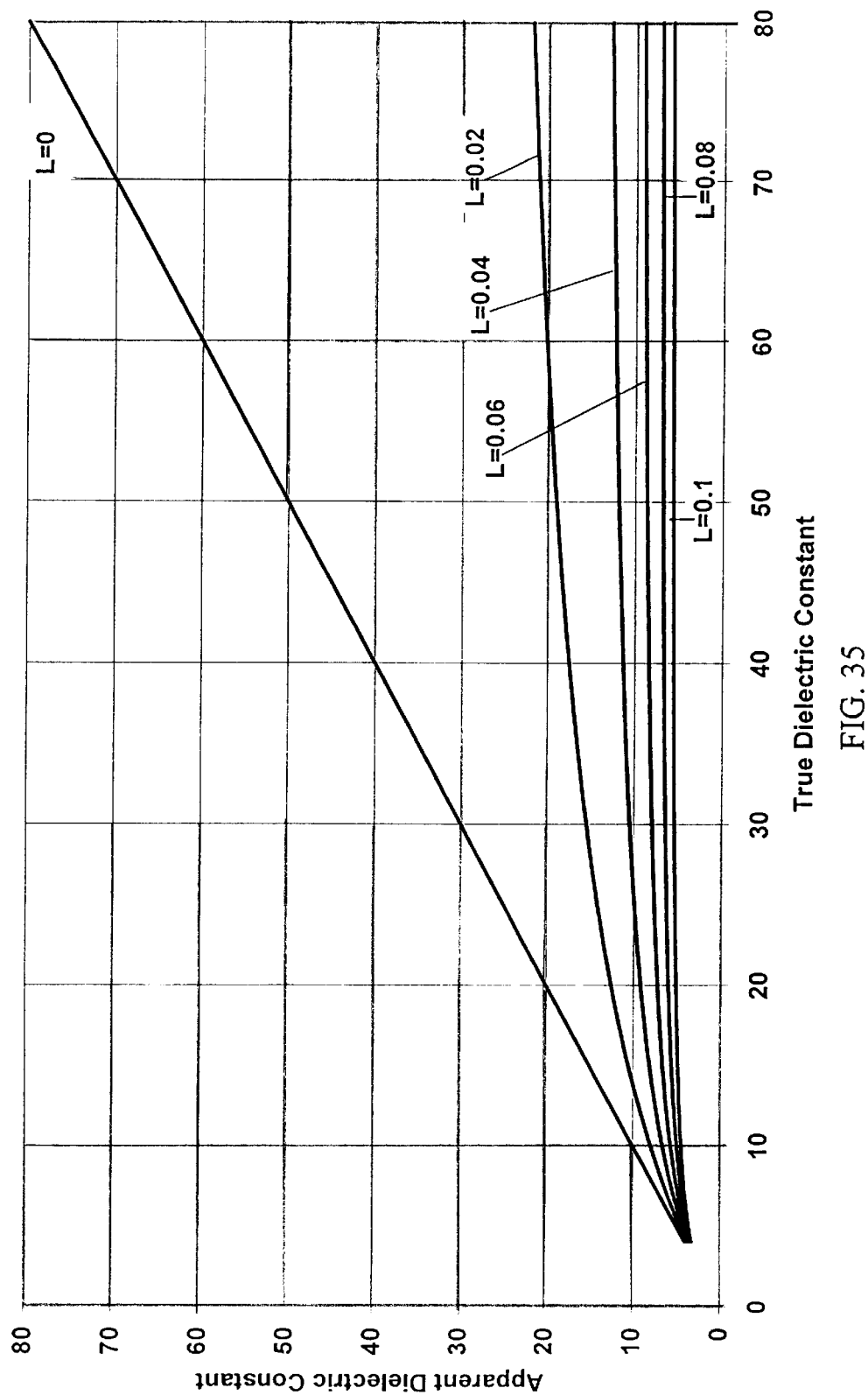

FIG. 21 shows cross section 21 of the alternate configuration of the device showing the outer transition body 70b, inner transition body 74b, alternate spacer 75b, and encapsulating resin 67.

The urethane resin forms a thick layer covering the outside of the inner conductor and the inside of the outer conductor. From the point of view of electric fields, a coating made from any non-conducting dielectric material would suffice. Urethane is used here because it has beneficial wear and structural properties. The purpose of these layers, particularly the layer covering the inner conductor, is to occupy the region of most sensitivity of the coaxial structure. FIG. 9 illustrates that a portion of fluid flowing through the device will contribute to the overall dielectric constant with a weighting that is dependent on the location of the portion of fluid within the device. When the outer diameter of the inner conductor is much smaller than the inner diameter of the outer conductor a portion of fluid occupying the region of space next to the inner conductor contributes to the overall average dielectric constant with a weighting much greater than a portion of fluid of the same volume occupying a region of space next to the outer conductor. If all of the fluid occupying the annular gap were homogeneously mixed then this would not be a problem. When dealing with fluids comprised of a mixture of oil and water, however, the walls of the annular gap get coated with a layer of oil whose thickness varies depending on difference in viscosity and density between the oil and water, and total flow rate. Under certain conditions the coating of oil surrounding the inner conductor can have an appreciable thickness. It is possible that this coating can occupy the majority of the high sensitivity region near the inner conductor. This can effectively isolate the coaxial structure from changes in the fluid that flows around the coating. Even if the coating does not occupy the entire area of high sensitivity, it will seriously affect the calibration of the device. If the region of high sensitivity around the inner conductor is occupied by urethane, whose dielectric constant remains fixed, the oil coating is pushed out of the region of high sensitivity and into a region where the sensitivity is closer to that of the remaining regions. This will reduce the effect the coating has on the calibration of the device.

The effect the layer of oil has on the calibration of the device can be estimated for the coaxial transmission line core as follows. Assuming that the oil/water mixture flowing through the annular gap of the coaxial transmission line core is thoroughly mixed, Knight shows that the weighting function is given by $$W(r,\phi) = (2*\pi*\ln(r2/r1))^{-1} * r^{-2} \quad (1)$$

where:
  r2=the inside diameter of the outer conductor of the coaxial core
  r1=the outside diameter of the inner conductor of the coaxial core
  r=the distance from the axis of the coaxial core of the point at which the weighting is calculated
  $\phi$=the angle about the axis of the coaxial core of the point at which the weighting is calculated As the system has cylindrical symmetry, equation (1) can be integrated about the axis of the coaxial core to produce a weighting function for an infinitesimally thin cylinder of material $$W(r) = (\ln(r2/r1)*r)^{-1} \quad (2)$$

Assuming that the thickness of the urethane coating over the outside of the inner conductor is the same as the thickness of the urethane coating on the inside of the outer conductor, and the thickness of the oil layer coating the outside of the urethane covered inner conductor is the same as the thickness of the oil layer coating the inside of the urethane covered outer conductor, equation (2) can be integrated with respect to r to determine the fraction of total weighting contained in the oil layers. Let t equal the thickness of one of the oil layers and L equal the thickness of one urethane coatings. Then the fraction of weighting contained within the space occupied by the oil layers is given by $$\left[\int_{r1+L}^{r1+L+t} \frac{1}{\ln\left(\frac{r2}{r1}\right) \cdot r} dr\right] + \left[\int_{r2-L-t}^{r2-L} \frac{1}{\ln\left(\frac{r2}{r1}\right) \cdot r} dr\right] = \frac{\ln\left[\frac{(r_2-L)}{(r_2-L-t)} \cdot \frac{(r_1+L+t)}{(r_1+L)}\right]}{\ln\left(\frac{r2}{r_1}\right)} \quad (3)$$

The maximum fraction of total weighting contained within the annular gap is given by $$\int_{r1+L}^{r2-L} \frac{1}{\ln\left(\frac{r2}{r1}\right) \cdot r} dr = \frac{\ln\left(\frac{r_2-L}{r_1+L}\right)}{\ln\left(\frac{r_2}{r_1}\right)} \quad (4)$$

The maximum total weighting in the annular gap occurs with L=0. In this case (4) reduces to $$\frac{\ln\left(\frac{r_2-L}{r_1+L}\right)}{\ln\left(\frac{r_2}{r_1}\right)} = 1 \quad (4a)$$

When L>0 then (4) gives a result less than 1. For a given L, (4) gives the maximum fraction of the total weighting that is available to the device for measurement purposes. Even though the maximum fraction is less than one a useful device can still be fashioned. When the annular gap is filled with dry oil the devices' calibration is adjusted to read zero water content. When the annular gap is filled with water the devices' calibration is adjusted to read 100% water content.

Dividing (3) by (4) gives PMFTW, the portion of maximum fraction of total weighting occupied by the oil layers.

$$PMFTW = \frac{\ln\left[\frac{(r2-L)}{(r2-L-t)}\right] \cdot \left[\frac{(r1+L+t)}{(r1+L)}\right]}{\ln\left[\frac{(r2-L)}{(r1+L)}\right]} \quad (5)$$

If r1, L, t, and r2 are expressed as a fraction of r2 then a family of normalized curves can be generated. FIG. 22 through FIG. 28 show a sequence of a family of curves generated by (5). Each figure shows a family of curve for a particular ratio of radii r1/r2. Each curve in the family shows the relationship between PMFTW and oil layer thickness (t) for a given urethane coating thickness (L). It is desirable to select a curve that has the smallest slope. This is the curve that will give the smallest PMFTW for a given thickness of oil layer and this, in turn, will produce the smallest error for that oil layer thickness.

Studying FIG. 22 through FIG. 28, it becomes apparent that there is a range of ratio of radii and urethane thickness that produce a curve with minimum slope. For a ratio of radii greater than ~0.15, adding a urethane layer only increases the slope curves. For a ratio of radii less than ~0.15, adding a urethane layer provides a benefit for layers up to a certain thickness. Beyond that, increasing the thickness also increases the slope of the curve. For a ratio of radii less than ~0.15, the smaller the ratio of radii, the larger the thickness of urethane required to minimize the slope of the curve.

The maximum error due to the presence of an oil layer can be estimated from (5). A particular device will have a particular ratio of radii and urethane thickness. Entering these values into (5) gives an equation for PMFTW vs. oil layer thickness (t). The fluid dynamic properties of the oil/water mixture, most notably the viscosity of the oil and the flow rate of the mixture, govern the thickness of the oil layer. For a given oil layer thickness PMFTW can be calculated. For example, a PMFTW=0.05 can be interpreted as follows: If the device initially had oil flowing through it and then the flow stream changed to 100% water but left an oil layer of thickness t coating the inside of the device, causing PMFTW=0.05, then instead of the device reading 100% it would read 95%. The oil layer prevents the water from filling 100% of the available measuring volume within the device and thus lowers the devices reading. This error is the maximum error because as the flow stream continued to flow 100% water the oil layer would gradually thin out allowing the water to occupy more of the available measuring volume of the device so the device reading would gradually increase from 95% to 100%.

In addition of reducing the effect that oil layers have on the calibration of the device, the urethane layer also provides a means for the device to deal with oil/water mixtures in which the water component contains significant amounts of dissolved salts. These dissolved salts cause the water portion of the mixture to become conductive. The amount of conductivity in the water is related mostly to the temperature of the fluid and the amount of salts dissolved in the water. Pressure has an affect of the conductivity as well but it is much less pronounced that temperature.

When the oil/water mixture is in the oil continuous phase (water droplets suspended in oil) the conductivity of the water does not make a large contribution to the overall bulk conductivity of the fluid because electric current is not able to flow from drop to drop through the oil. When the oil/water mixture is in the water continuous phase (oil droplets suspended in water) the bulk conductivity of the mixture is greatly influenced by the conductivity of the water component. At moderate to high bulk fluid conductivities, the fluid will absorb the electromagnetic pulse propagating along the coaxial transmission line. This will degrade the operation of the device, sometimes to the point where the device stops working. The addition of a thick dielectric coating removes the conductive fluid from the region of high sensitivity near the inner conductor and reduces the influence of the conductive fluid in the same manner as it reduces the influence of oil layers.

The addition of any dielectric coating to the conductors of the coaxial structure reduces the sensitivity to changes in the dielectric constant of the fluid flowing through the coaxial structure. The effect of the dielectric coating is to partially shield the coaxial structure from the dielectric of the fluid. Thus, the dielectric constant of the fluid apparent to the coaxial structure differs from the true dielectric constant of the fluid, the difference being determined by thickness of the dielectric coating and the ratio of radii. Annan has derived an expression relating the apparent dielectric constant, $K_{apparent}$, to the true dielectric constant, $K_{fluid}$, for a coaxial structure. The relationship is reproduced here in terms of r1, r2, and L.

$$K_{apparent} = F \cdot K_{fluid} \quad (6)$$

where $$F = \frac{\frac{K_{dc}}{K_{fluid}} \cdot \ln\left(\frac{r2}{r1}\right)}{\ln\left(1 + \frac{L}{r1}\right) + \frac{K_{dc}}{K_{fluid}} \cdot \ln\left(\frac{r2-L}{r1+L}\right) + \ln\left(\frac{r2}{r2-L}\right)} \quad (7)$$

and $K_{dc}$=dielectric constant of the dielectric coating

FIG. 29 through FIG. 35 show a sequence of a family of curves depicting (6) for various ratio of radii and various dielectric thicknesses, L. This sequence of curves has the same choices of ratio of radii and L as FIG. 22 through FIG. 28 for comparison purposes.

As would be intuitively expected there is a 1 to 1 correspondence between the apparent dielectric constant and the true dielectric constant when L=0. Adding even a small dielectric coating significantly reduces the sensitivity of the coaxial structure. A thicker dielectric coating produces a lower the sensitivity. Studying FIG. 29 through FIG. 35 and (6), it becomes apparent that for a given thickness of dielectric coating, the sensitivity is reaches a maximum for a certain ratio of radii. A relationship for ratio of radii that maximizes the sensitivity can be derived by differentiating (6) with respect to r1 to give $$\frac{d}{dr1} K_{apparent} = \quad (8)$$

$$\frac{K_{dc}}{r1 \cdot K_{fluid}} \cdot \left[ \frac{\ln\left(\frac{r2}{r1}\right) \cdot (L \cdot K_{fluid} + r1 \cdot K_{dc})}{(r1+L) \cdot \left(\ln\left(1 + \frac{L}{r1}\right) + \frac{K_{dc}}{K_{fluid}} \cdot \left(\frac{r2-L}{r1+L}\right) + \ln\left(\frac{r2}{r2-L}\right)\right)^2} - \right.$$

-continued $$\frac{K_{fluid}}{\ln\left(1+\frac{L}{r1}\right)+\frac{K_{dc}}{K_{fluid}}\cdot\ln\left(\frac{r2-L}{r1+L}\right)+\ln\left(\frac{r2}{r2-L}\right)}\Bigg]$$

Setting (8) equal to zero gives the relationship $$\frac{\ln\left(\frac{r2}{r1}\right)\cdot(L\cdot K_{fluid}+r1\cdot K_{dc})}{K_{fluid}\cdot(r1+L)\cdot\left(\ln\left(1+\frac{L}{r1}\right)+\frac{K_{dc}}{K_{fluid}}\cdot\ln\left(\frac{r2-L}{r1+L}\right)+\ln\left(\frac{r2}{r2-L}\right)\right)}=1 \quad (9)$$

which must be satisfied for the sensitivity to be maximized. Generally this maximum occurs for ratio of radii less than 0.3 and depends on the chosen thickness for the dielectric coating, L, and is independent of the dielectric constant of the fluid.

A procedure for selecting a dielectric coating thickness and ratio of radii can be suggested from the above discussion. The first parameter to be selected is the dielectric coating thickness. There are two issues to consider when selecting a thickness, oil layer thickness and bulk conductivity.

The viscosity of crude varies depending on the geologic formation from which it is pumped. Light crude oil has a lower viscosity than heavy crude oil. High viscosity oils tend to make thicker layers on the inner walls of the device than low viscosity oils for two reasons. Firstly, for a given flow rate, the high viscosity oil will be harder to flush off the walls of the device and will lead to thicker layers. These layers will take longer to thin out relative to a low viscosity oil layer. Secondly, high viscosity oils are generally pumped at a lower flow rate due to their higher viscosity. This initially leads to even thicker layers, and longer times to thin out the layer. The most likely layer thickness must be determined using experimental or theoretical means.

Once this thickness has been determined, the maximum tolerable PMFTW should be selected. This is chosen based on the performance requirements for the device, i.e. if the device accuracy is specified as +/−5% then the maximum PMFTW would be 0.05. Equation (5) or FIG. 26 through FIG. 32 are consulted to select a curve that does not exceed the allowed value of PMFTW of the chosen oil layer thickness. There may be more than one curve satisfying this condition. Select the curve that gives the largest value of L. Once L has been selected use (9) to determine the optimum ratio of radii.

Also, L should be sufficiently thick to permit the device to operate when filled with a fluid that has a bulk electrical conductivity as large as the largest bulk electrical conductivity expected in the normal operation. It is known from experimentation that a ratio of radii=0.4 and L=0.1 and an electrode length=14.4*r2 allows the device to continue to operate with fluids having a bulk electrical conductivity of 130 dS/m.

The electronics operate as follows, referring to FIG. 2 and FIG. 10: Once electric power is supplied to the device the microprocessor 10 triggers one pulse from the pulse generator 7. This pulse passes through the line driver 8 to amplify it. The pulse then travels along a standard coaxial cable 5b until it meets the core 5. The pulse then travels through the core. The water content of the fluid in and around the core at the time of the pulse's arrival will affect the travel time of the pulse through the core. The pulse then travels through another standard coaxial cable 5a back to a comparator 6. If the height of the received pulse is higher than the adjustable reference then the comparator 6 triggers the pulse generator 7 to generate the next pulse. From this point, barring any changes in the signal degradation as the pulse passes through the core 5, the circuit self-generates a continuous series of pulses without the need for the microprocessor to intervene. The round trip time of each pulse is the sum of the travel time through the core which varies with water content and the travel time through the rest of the circuit which, in principle, remains constant. With the aid of the reference oscillator 12, the timing circuit 11 measures the total round trip time of the pulse and reports this time to the microprocessor 10.

An ideal pulse generator would generate a pulse that had an infinitely fast rise time and an infinitely fast fall time and would produce a pulse shaped A as shown in the dashed line of FIG. 3. In the real world the rise and fall times of the pulse are not infinite and the shape of the pulse is more like that shown in the solid line B of FIG. 3.

When a real pulse passes through the core, while the core contains a real fluid, the rise time of the pulse received by the electronics is lengthened due to preferential absorption of the higher frequency components of the pulse by the fluid. FIG. 4 compares the pulse shape B prior to passage through the core 5 to the pulse shape C after passage through the core 5. The amount of increase in the rise time of the pulse is related to the water content of the fluid passing through the annular gap 63, the bulk electrical conductivity of this fluid, and the length of the conductors 48 and 57 of the core 5.

Referring to FIG. 2 and FIG. 10, while in normal operation the comparator 6, pulse generator 7, and the line driver 8 act in concert to generate a continuous series of pulses that travel through the core. The timing circuit 11 and reference oscillator 12 act in concert to measure the period of oscillation of the series of pulses being generated by the pulse generator 8. The timing marker used for this measurement is the point at which the rising edge of the pulse crosses the level of the adjustable reference 9 at the comparator 6. The timing circuit 11 measures the time interval between successive crossings.

FIG. 5 shows the timing relationship between the timing markers and the measured time interval between crossings. The top waveform represents output of the line driver 8. The bottom waveform represents the signal received by the comparator 6. For the purpose of this description it is assumed that the propagation delay times of comparator 6, pulse generator 7, and line driver 8 are nil. These delays will be dealt with at the end of this discussion. The microprocessor 10 causes the pulse generator 7 to generate the first pulse 19 from the line driver 8. This pulse propagates through a cable 5b, the core 5, and another cable 5a, to reach the comparator 6. By the time the pulse reaches comparator 6 it has changed shape 20 due to preferential attenuation of the higher frequency components. This attenuation occurs to a small degree in cables 5a and 5b but the majority of the attenuation occurs in the core 5. The comparator triggers the generation of another pulse when the level of the rising edge of pulse 20 crosses the level of the other comparator input, which is set by the adjustable reference 9. Because the rising edge of pulse 20 takes time to complete its transition, changing the reference level will cause the crossing to occur at different times relative to the beginning of pulse 19. Alternatively, if the adjustable reference is set to the level indicated by 14, for example, it can be seen from FIG. 6 that if the rise time of the received pulse changes, the time at which the crossing occurs will also change. Changes in the crossing time, relative to the beginning of pulse 19, caused by changing the reference or by the changing rise time of the received pulse can be a significant portion of the total period 16, 17, 18, 25, or 26. For this reason it is desirable to take account of these changes.

FIG. 5 also depicts a method for removing most or all of the change in period caused by the varying rise time of the received pulse. The method proceeds as follows:

1) Set the adjustable reference level to a point that is near the baseline 22 of the received pulse 20 but far enough above it to ensure reliable sing-around operation. For example set the adjustable reference to 13.
2) Measure the period of oscillation 16 associated with the reference level 13.
3) Now set the adjustable reference level to a higher level, 14 for example.
4) Measure the period of oscillation 17 associated with reference level 14.
5) Fit an analytical curve to the data points obtained in steps 1 to 4. Steps 3 and 4 will need to be repeated as many times as necessary to obtain the minimum number of points required to allow the curve fitting procedure to proceed.
6) Use the analytical curve derived in step 5 to extrapolate what the period of oscillation would have been if the reference level could have been set equal to the baseline 22 of the received pulse 20. The period of oscillation obtained by this extrapolation is much less sensitive to changes in the rise time of the received pulse.

The type of curve used in step 5 can be a line, a polynomial, an exponential or any other curve that can be used to represent the shape of the rising edge of the received pulse 20. If the reference levels are selected judiciously, as illustrated in FIG. 5 for 13 and 14, then the line 23 provides a simple curve that can accurately estimate the intersection 24 of the baseline 22 of the received pulse with the beginning of the rising edge of the pulse 20. When computational power is limited it is preferable to use as simple a curve fitting procedure as possible. If sufficient computational power is available then using a higher order polynomial or exponential curve will provide a more accurate estimate of the intersection 24.

In addition to determining the intersection 24, the slope of the line 23 can also be determined. This slope can be used to infer the bulk electrical conductivity of the fluid flowing through the device. FIG. 8 shows the relationship between the rise time of pulse 20 and the bulk electrical conductivity of the fluid passing through the device. The exact form of FIG. 8 depends not only on the bulk conductivity of the fluid passing through the core 5 of the device, but also the cabling details connecting the core 5 to the electronics as well as the exact geometric configuration of the core. Once these parameters are fixed in a particular device design, however, the form of FIG. 8 can be determined for that design and used to relate rise time to bulk conductivity.

Earlier in this discussion it was assumed that the propagation delay times of the comparator 6, pulse generator 7, and line driver 8 were negligible. In reality this is not the case. The existence of a propagation delay through the electronics changes the timing relationship to that shown in FIG. 7. The sum of the propagation delay times of the comparator 6, pulse generator 7, and line driver 8 is given by 27. The new period of oscillation of the sing-around circuit becomes 17 plus 27. If the total propagation delay 27 were a constant value, its presence would have little effect on the overall system performance. This propagation delay, being the sum of the propagation delays of individual components, will be subject to any variations within each of these components. These variations can occur due to a change in temperature of an individual component or just random drift. These variations show up directly in the measurement of the period of oscillation, and so, can be a significant source of error in the measurement.

The circuit shown in FIG. 10 is a modified version of the circuit shown in FIG. 2. The modification involves placing single pole double throw RF switches 28a and 28b in the transmission lines 5a and 5b respectively, and connecting a reference transmission line 29 from the extra throw of 28a to the extra throw of 28b. The microprocessor 10 controls the position of both RF switches. Alternatively, the switches 28a, 28b could be placed elsewhere in the circuit, providing that electrical components in the circuit shown in FIG. 2 are matched by the equivalent components in the reference circuit. For example, there could be a separate comparator, pulse generator and line driver for the reference transmission line. The following method can be used to correct the measured period of oscillation of the sing-around circuit for variations in the propagation delay time through the electronic components.

Periodically the microprocessor sets the RF switches to connect the reference transmission line 29 to the sing-around circuit rather than the core 5. The sing-around circuit is operated to determine its period of oscillation. This value is stored as an offset reference by the microprocessor 10. The microprocessor then switches the core 5 back into the sing-around circuit.

The reference transmission line 29 will contribute a propagation delay to the overall period of oscillation that is proportional to its length. The length of 29 will vary with temperature but the change in length as a percent of the total length of 29 will be negligible over the temperature range of interest. Therefore it is assumed that the length of 29 and hence the propagation delay through 29 remains constant.

The offset reference stored by the microprocessor includes the propagation delays from 29 and the electronics. This offset reference is subtracted from the period measurements of the sing-around circuit while the core 5 is being measured. As drift in the electronics causes the propagation delay through the electronics to increase, the period of oscillation measured by the sing-around will increase. The offset reference will increase by the same amount. By subtracting the offset reference from the period measurement, the influence of electronic drift has been removed. The frequency at which the offset reference is updated can be selected to suit the application. For instance, if temperature fluctuations in the devices' surroundings are slow the update rate can be made slower, lowering the system overhead requirements.

FIG. 11 shows a second detection apparatus and method for the device. In this detection apparatus a free running oscillator 31 generates a square wave output and oscillates at a preset frequency. The output of 31 is simultaneously fed to line drivers 8a and 8b. The output from line driver 8a is fed to the core 5 of the device and then to the comparator 6a The output from line driver 8b is fed to the reference transmission line 30 and then to comparator 6b. The signal arriving at comparator 6a is compared with the output of the adjustable reference 9a, which, in turn, is controlled by the microprocessor 10. When the level of the signal is above the level of the adjustable reference the output of the comparator 6a is high, otherwise the output of the comparator is low. Similarly for comparator 6b, the level of the signal from the reference transmission line 30 is compared to the level of the adjustable reference 9b, which, in turn, is controlled by the microprocessor 10. When the level of the signal from 46 is above the level of the adjustable reference 9b then the output of the comparator is high otherwise the output of the comparator is low.

The outputs of comparator 6a and 6b are fed into an exclusive OR device 32. This device produces a high output if the output from 6a and 6b differ. If the outputs from 6a and 6b are either both high or both low the output of 32 is low.

The time relationship between these signals is shown in FIG. 12. The output of the free running oscillator is trace J. The outputs of both line drivers change state simultaneously, some short delay time after the output of the oscillator changes state. The output of line driver 8a is shown in trace K and the output of line driver 8b is shown in trace L. Line driver 8a feeds its signal to the core 5 of the device and then to comparator 6a. The output for 6a is shown in trace M. Line driver 8b feeds its signal to the reference transmission line 30 and then to comparator 6b. The output for 6b is shown in trace N. The length of 30 is adjusted so that when the fluid flowing through the core 5 of the device has the lowest dielectric constant that is expected during normal operation, the output of comparator 6b is coincident with the output of comparator 6a. As the dielectric constant of the fluid flowing through the core 5 increases, the propagation delay of the signal through the core increases. Thus the change of state of the output of comparator 6a occurs at a time later than that of comparator 6b. The output of the exclusive OR is shown in trace O. This output shows a pulse whose width is directly related to the dielectric constant of the fluid passing through the core. Thus the output of 32 is essentially a pulse width modulated signal.

The output of exclusive OR 32 is fed into 33, which is a pulse width demodulator. The details of this circuit are not important to the description of this invention. There are a number of standard methods for converting a pulse width modulated signal into a base band signal. For example, provided the amplitude of the pulses is stable a simple resistance-capacitance low-pass filter is sufficient to filter the pulses and produce a DC voltage that is proportional to the pulse width. The base band signal can then be passed on to the microprocessor 10 for further processing. Alternatively, 32 and 33 may be replaced with any apparatus that can measure the time interval between the transition of trace N and the corresponding transition of trace M.

An alternate configuration of the device is possible utilizing a parallel conductor transmission line rather than a coaxial transmission line. FIGS. 17A and 17B show the plan view and end view of a device using this alternate configuration. FIG. 18A and FIG. 18B shows a longitudinal cross section of this device. The urethane potting 67 is molded in such a way as to create a fluid passage of circular cross section 69 with conical inlet and outlet transition sections, 68a and 68b. The reduced cross sectional area of the fluid passage 69, compared to the inlet pipe diameter, of this particular arrangement, is useful in applications where the flow rate is very low. The flow velocity through the passage 69 will be greater than the flow velocity of the inlet pipe. This feature helps keep the oil/water mixture mixed as it flows through the passage. The diameter of the passage 69 can be selected based on the flow rate of the application. Also shown in the cross section of FIG. 18A and FIG. 18B are the alternate spider assemblies. FIG. 18A and FIG. 18B shows that the alternate spider assembly is similar in nature to the spider assemblies in FIG. 14A and FIG. 14B. The alternate assembly consists of an outer transition bodies 70a, and 70b, an alternate spacers 72a and 72b, an alternate washers 75a and 75b, an alternate o-rings 76a and 76b, and inner transition bodies 74a and 74b from the center conductor to one of the parallel conductors of the transmission line. FIG. 20 shows the cross section 20 that illustrates the transition from the spider assembly to the parallel conductor of the transmission line. This view shows the outer transition body 70b, the fluid passage 69, the urethane potting 67, as well as the inner transition body 74b to the other parallel conductor of the transmission line. FIG. 21 shows cross section 21 of the alternate spider assembly. FIG. 19 shows cross section 19 of the alternate device. The circular fluid passage 69, the urethane potting 67, and both of the conductors, 77a and 79b, of the parallel conductor transmission line are shown.

As mentioned previously, the cross sectional area of the fluid passage 69 can be changed to accommodate various flow rates. Further, the shape and size of the parallel conductors 77a and 77b can be changed relative to the fluid passage 69 in order to maximize the interaction of the electric field between the parallel conductors and the fluid contained in the passage 69. Further, the cross sectional shape and size of passage 69 relative to the parallel conductors can be change to further increase the interaction of the electric field between the parallel conductors with the fluid in the passage.

The size of passage 69 relative to the parallel conductors could be such that the conductors were contained within the passage and the fluid flowing through the passage completely surrounded both conductors. In this situation there is an effect that is similar to the case of the coaxial transmission line geometry. In the parallel conductor geometry, the electric field strength is highest near the conductors and diminishes rapidly as the distance from the conductors increases. Thus the fluid close to the conductors makes a disproportionately large contribution to the overall measurement at the expense of the fluid further away from the conductors. Therefore, it is possible for thick oil coatings on the conductors to shield the conductors from the affects of water elsewhere in the passage, rendering the device ineffectual in measuring the water content of the fluid. Therefore, the device shown here has the area immediately surrounding the conductors occupied by urethane potting. Also the fluid is confined to the area between the conductors, where the highest electric field strength exists.

In the preferred embodiment, ECL (emitter coupled logic) is used to generate a pulse with a voltage of +0.68 volts (baseline of −1.6 volts). If CMOS technology is used, the pulse may be 5 volts, baseline 0 volts. Pulse duration may be about 0.5 to about 15 nanoseconds. For when an oscillating circuit is used, frequencies in the range of 5–25 MHz are believed to be desirable, with a duty cycle of about 20% to 80%. For setting of the adjustable reference, a useful starting point is −0.9 volts, and then initially increasing and then decreasing the setting until sufficient information is gained to extrapolate the time interval to its value at the baseline voltage.

Immaterial modifications to the invention described here will occur to those skilled in the art, and are intended to be included within the scope of the invention.

The embodiments of the invention in which an exclusive property or privilege is claimed are defined as follows:

1. A sensor for measuring the dielectric constant of a fluid, the sensor comprising:
   a conduit for the fluid, the conduit having first and second ends, between which electrical energy may pass;
   an electrical generator having as output an electrical transient, the electrical generator being operably connected to the conduit for transmitting the electrical transient along the conduit, wherein propagation of the electrical transient is affected by the fluid, the electrical transient having a rise time;

a receiver connected to the conduit for detecting electrical transients that have passed along the conduit from the electrical generator; and a processor operably connected to the electrical generator and to the receiver, the processor being programmed to cause the electrical transient to be generated by the electrical generator for passage along the conduit and determine the dielectric constant of the fluid from, the propagation time of the electrical transient detected at the receiver being adjusted to remove variability of the propagation time caused by the rise time of the electrical transient.

2. The sensor of claim 1 in which the electrical generator and the receiver are located at opposed ends of the conduit.

3. The sensor of claim 2 in which the electrical generator generates a further electrical transient upon receipt of an electrical transient at the receiver for input into the conduit, thereby forming a sing-around circuit, and the sensor further comprises a timing circuit for measuring the oscillation period of the sing-around circuit, the timing circuit being configured to output a timing signal to the processor.

4. The sensor of claim 3 in which the transmission line is formed from co-axial inner and outer conductors, and has an annulus between the inner and outer conductors, with fluid to be measured filling the annulus.

5. The sensor of claim 4 in which the inner conductor is coated with electrical insulation.

6. The sensor of claim 5 in which the electrical insulation extends a distance into the annulus sufficient to exclude fluid being measured from areas of greatest electric field intensity.

7. The sensor of claim 4 in which the ratio of the diameter of the outside of the inner conductor to the diameter of the inside of the outer conductor is greater than 0.2.

8. The sensor of claim 2 in which the transmission line, the electrical generator and the receiver together form a sensing circuit, and the sensor further comprising:

a reference circuit having a similar propagation delay to the sensing circuit apart from the effect of the dielectric constant of the fluid being measured on the transmission of electrical transients along the transmission line; and the processor being configured to determine the dielectric constant of the fluid taking into account delay of tie electrical transient due to passage through electrical components that are common to both the sensor and the reference circuit.

9. The sensor of claim 8 in which the receiver comprises a comparator for comparing the voltage level of signals received by the receiver with an adjustable threshold, the propagation time of the electrical transient being determined from the time at which the voltage level of signals received by the receiver exceeds the threshold.

10. The sensor of claim 9 in which the processor is programmed to:

A) adjust the adjustable threshold to a value that is below the maximum voltage level of the electrical transient received by the receiver;

B) determine the travel time of the electrical transient along the transmission line for the adjusted value of the adjustable threshold;

C) repeat steps A and B for different values of the adjustable threshold to form a set of data pairs comprising the adjustable threshold and the travel time for each setting of the adjustable threshold; and D) determine the dielectric constant of the fluid being measured from the data pairs.

11. The sensor of claim 10 in which the processor is programmed to:

find a curve that matches the data pairs; and determine the dielectric constant of the fluid being measured from an extrapolation of the curve at a travel time corresponding to the base line of the electrical transient.

12. The sensor of claim 11 in which the processor is programmed to correct the dielectric constant using a determination of the bulk conductivity of the fluid from the slope of the rising edge of the electrical transient.

13. The sensor of claim 9 in which the reference circuit comprises a second comparator for comparing the voltage level of signals received by a second receiver with the adjustable threshold, the time of arrival of an electrical transient at the second receiver being the time at which the voltage level of signals received by the second receiver exceeds the adjustable threshold.

14. The sensor of claim 9 in which the conduit is contained within a pressure container for withstanding pressure inside an oil pipeline.

15. The sensor of claim 9 in which the transmission line comprises first and second parallel side-by-side conductors separated by a gap, the gap being substantially filled by the fluid to be measured.

16. The sensor of claim 15 in which the first and second parallel conductors are coated with electrical insulation.

17. A sensor for determining a property of a fluid, the sensor comprising:

a transmission line extending between a first end and a second end, the transmission line being defined by co-axial inner and outer conductors, the inner and outer conductors being spaced apart to define a gap through which gap a fluid may flow;

an electrical generator connected to the first end of the transmission line at multiple connection points spaced around the transmission line for transmitting electromagnetic energy into the transmission line, the spacing of the multiple connection points being configured for preferentially suppressing higher order modes of propagation of the electromagnetic energy along the transmission line;

a receiver operably connected to the transmission line for receiving electromagnetic energy that has passed along the transmission line from the electrical generator; and a processor connected by first and second communication links respectively to the electrical generator and the receiver for processing signals received by the receiver and for generating a signal indicative of a property of fluid confined within the gap from signals received by the receiver that have passed along the transmission line.

18. The sensor of claim 17 in which the property is the dielectric constant of the fluid, and the processor is programmed to calculate the dielectric constant of the fluid from the time of flight of electrical signals along the transmission line.

19. The sensor of claim 18 in which the multiple connection points comprise;

first and second feed lines, the first feed line being electrically connected to the inner conductor, and the second feed line being electrically connected to the outer conductor; and the second feed line being electrically connected to the outer conductor at multiple positions around the outer conductor.

20. The sensor of claim 19 in which the second feed line is electrically connected to the outer conductor at least at three positions.

21. The sensor of claim 20 in which the at least three positions are spaced uniformly around the outer conductor.

22. The sensor of claim 21 in which the first and second feed lines together form a co-axial cable.

* * * * *